US006294336B1

(12) United States Patent
Boyce-Jacino et al.

(10) Patent No.: US 6,294,336 B1
(45) Date of Patent: Sep. 25, 2001

(54) METHOD FOR ANALYZING THE NUCLEOTIDE SEQUENCE OF A POLYNUCLEOTIDE BY OLIGONUCLEOTIDE EXTENSION ON AN ARRAY

(75) Inventors: Michael T. Boyce-Jacino, Finksburg; Yu-Hui Rogers, Damascus; Philip Goelet, Reisterstown, all of MD (US)

(73) Assignee: Orchid Biosciences, Inc., Princeton, NJ (US)

(*) Notice: Subject to any disclaimer, the term of this patent is extended or adjusted under 35 U.S.C. 154(b) by 0 days.

(21) Appl. No.: 09/522,494

(22) Filed: Mar. 9, 2000

Related U.S. Application Data

(63) Continuation of application No. 08/616,906, filed on Mar. 19, 1996, now abandoned.

(51) Int. Cl.⁷ ................ C12Q 1/68; C12P 19/34
(52) U.S. Cl. ................ 435/6; 435/91.1
(58) Field of Search ................ 435/6, 91.1, 810

(56) References Cited

U.S. PATENT DOCUMENTS

| | | | |
|---|---|---|---|
| 4,307,189 | 12/1981 | Kit | 435/6 |
| 4,563,419 | 1/1986 | Ranki et al. | 435/6 |
| 4,656,127 | 4/1987 | Mundy et al. | |
| 4,683,195 | 7/1987 | Mullis et al. | 435/6 |
| 4,760,017 | 7/1988 | McCormick | 435/6 |
| 4,851,331 | 7/1989 | Vary et al. | 435/6 |
| 4,883,750 | 11/1989 | Whiteley et al. | 435/6 |
| 4,962,020 | 10/1990 | Tabor et al. | 435/6 |
| 4,968,602 | 11/1990 | Dattagupta | 435/6 |
| 5,002,867 | 3/1991 | Macevicz et al. | |
| 5,200,314 | 4/1993 | Urdea | 435/6 |
| 5,429,807 | 7/1995 | Matson et al. | |

(List continued on next page.)

FOREIGN PATENT DOCUMENTS

| | | |
|---|---|---|
| 0238332 | 9/1987 | (EP) . |
| 0246864 | 11/1987 | (EP) . |
| 0288737 | 11/1988 | (EP) . |
| 0 297 379 A2 | 4/1989 | (EP) . |
| 0317074 | 5/1989 | (EP) . |
| 0332435 | 9/1989 | (EP) . |
| 0333465 | 9/1989 | (EP) . |
| 0357011 | 3/1990 | (EP) . |
| 0370694 | 5/1990 | (EP) . |
| 0371437 | 6/1990 | (EP) . |
| 2650840 | 2/1991 | (FR) . |
| 2202328 | 9/1988 | (GB) . |
| WO 86/03782 | 7/1986 | (WO) . |
| WO 89/09282 | 10/1989 | (WO) . |
| 8910414 | 11/1989 | (WO) . |
| 8910977 | 11/1989 | (WO) . |
| WO 90/01069 | 2/1990 | (WO) . |
| WO 90/06042 | 6/1990 | (WO) . |
| 9009455 | 8/1990 | (WO) . |
| WO 90/11372 | 10/1990 | (WO) . |
| 9102087 | 2/1991 | (WO) . |
| 9215712 | 2/1991 | (WO) . |
| WO 91/13075 A2 | 9/1991 | (WO) . |
| WO 91/13075 A3 | 11/1991 | (WO) . |
| WO 92/16657 | 10/1992 | (WO) . |
| WO 95/00669 | 1/1995 | (WO) . |

OTHER PUBLICATIONS

Ballabio et al., "PCR Test for Cystic Fibrosis Deletion", Nature, 343:220 (1990).
Caskey et al., "Disease Diagnosis by Recombinant DNA Methods"s, Science, 236:1223–1228 (1987).
Delius et al., "Separation of Complementary Strands of Plasmid DNA Using the Biotin–Avidin System and Its Application to Heteroduplex Formation and RNA/DNA Hybridizations in Electron Miscroscopy" Nucleic Acids Research 13: 5457–5469 (1985).
Ehlen et al., "Detection of Ras Point Mutations by Polymerase Chain Reaction Using Mutation–Specific Inosine–Containing Oligonucleotide Primers", Biochemical and Biophysical Research Communications, 160: 441–447 (1989).
Grimberg et al., "A Simple and Efficient Non–Organic Procedure for the Isolation of Genomic DNA From Blood", Nucleic Acids Research, 17:8390 (1989).
Hyman, E. D., "A New Method of Sequencing DNA", Analytical Biochemistry, 174:423–436 (1988).
Kerem et al., "Identification of the Cystic Fibrosis Gene: Genetic Analysis", Science, 245:1073–1080 (1989).
Kuppuswamy et al., "A New Use of Polymerase Chain Reaction (PCR) in Carrier Detection of Hemophilia–B Due to Point Mutations", Blood vol. 74 No. 7 (1989).

(List continued on next page.)

*Primary Examiner*—Kenneth R. Horlick
(74) *Attorney, Agent, or Firm*—Kalow & Springut LLP; David A. Kalow; William D. Schmidt

(57) ABSTRACT

The present invention provides a method for determining the nucleotide sequence of a nucleic acid molecule using primer oligonucleotides arrayed on a solid support and doing primer extension. By providing sequence information from both oligonucleotide primers in which the 3' terminal nucleotide of the oligonucleotide primer is hybridized to the nucleic acid molecule and oligonucleotide primers in which the 3' terminal nucleotide is not hybridized to the nucleic acid molecule the invention is advantageous in that less primers are needed to fully sequence a nucleic acid molecule. Where the 3' terminal nucleotide of an oligonucleotide in the array does not hybridize to the nucleic acid molecule, the present invention provides for either not permitting oligonucleotides hybridized to nucleic acid molecules to be extended by polymerase-mediated incorporation of a single chain terminator nucleotide residue onto the 3' terminus of said hybridized oligonucleotide, or permitting the removal of any non-hybridized nucleotide residues from the 3' terminus of said hybridized oligonuclcotides, so as to form a truncated primer oligonucleotide whose 3' terminus is hybridized to said nucleic acid molecule. The invention also provides kits that can be used to implement the methods of the invention.

31 Claims, 1 Drawing Sheet

U.S. PATENT DOCUMENTS

| | | |
|---|---|---|
| 5,436,327 | 7/1995 | Southern et al. . |
| 5,445,934 | 8/1995 | Fodor et al. .............................. 435/6 |
| 5,489,678 | 2/1996 | Fodor et al. ......................... 536/22.1 |
| 5,605,662 | 2/1997 | Heller et al. . |
| 5,744,305 | 4/1998 | Fodor et al. .............................. 435/6 |
| 5,763,263 | 6/1998 | Dehlinger ............................. 435/287 |
| 5,846,710 | 12/1998 | Bajaj ........................................ 435/6 |
| 5,846,719 | 12/1998 | Brenner et al. .......................... 435/6 |
| 5,856,092 | 1/1999 | Dale et al. ............................... 435/6 |
| 5,888,819 | 3/1999 | Goelet et al. ............................ 435/5 |
| 6,004,744 | 12/1999 | Goelet et al. ............................ 435/5 |
| 6,013,431 | 1/2000 | Soderlund et al. ....................... 435/5 |
| 6,153,379 | 11/2000 | Caskey et al. ........................... 435/6 |
| 6,156,501 | 12/2000 | McGall et al. ........................... 435/6 |

OTHER PUBLICATIONS

Landergren et al., "DNA Diagnostics–Molecular Techniques and Automation", Science, 242:229–237 (1988).

Landergren et al., "A Ligase–Mediated Gene Detection Technique",Science, 241:1077–1080 (1988).

Mikita et al., "Functional Consequences of the Arabinosylcytosine Structural Lesion in DNA", 27:4698–4705 (1988).

Mitchell et al., "Affinity Generation of Single Stranded DNA Following the Polymerase Chain Reaction: Application to Dideoxy Sequencing", WH 214 Journal of Cellular Biochemistry Supp. 13E 18th Annual Meeting (1989).

Mullis et al., "Specific Synthesis of DNA in Vitro Via a Polymerase–Catalyzed Chain Reaction", Methods in Enzymology, 155:335–351 (1987).

Mullis, K. B., "The Unusual Origin of the Polymerase Chain Reaction", Scientific American, 56–65 (1990).

Nassal et al., "PCR–Based Site–Directed Mutagenesis Using Primers With Mismatched 3'—Ends", Nucleic Acids Research, 18:3077–3078 (1990).

Newton et al., "Analysis of Any Point Mutation in DNA. The Amplification Refractory Mutation System (ARMS)", Nucleic Acids Research, 17:2503–2516 (1989).

Riordan et al., "Identification of the Cystic Fibrosis Gene: Cloning and Characterization of Complementary DNA", Science, 245:1066–1072 (1989).

Rommens et al., "Identification of the Cystic Fibrosis Gene: Chromosome Walking and Jumping", Science, 245:1059–1065 (1989).

Rossiter et al., "Molecular Scanning Methods of Mutation Detection", The Journal of Biological Chemistry, 265:12753–12756 (1990).

Running et al. "A Procedure for Productive Coupling of Synthetic Oligonucleotides to Polystyrene Microtiter Wells for Hybridization Capture" Biotechniques 8: 276–277 (1990).

Signer et al., "DNA Fingerprinting: Improved DNA Extraction From Small Blood Samples", Nucleic Acids Research, 16:7738 (1988); and Signer et al., "Modified Gel Electrophoresis for Higher Resolution of DNA Fingerprints", Nucleic Acids Research, 16:7739 (1988).

Smith, "DNA Sequence Analysis by Primed Synthesis", Methods in Enzymology, 65:560–581 (1980).

Spitzer et al., "Molecular Defect in Factor IXBm Lake Elsinore", The Journal of Biological Chemistry; 263:10545–10548 (1988).

Spritzer et al., "Replacement of Isoleucine–397 by Threonine in the Clotting Proteinase Factor IXa (Los Angeles and Long Beach Variants) Affects Macromolecular Catalysis but not L–tosylarginine Methyl Ester Hydrolysis", Biochem. J. 265: 219–225 (1990).

Syvanen et al., "Quantification of Polymerase Chain Reaction Products by Affinity–Based Hybrid Collection," Nucleic Acids Research, 16:11327–11339 (1988).

Syvanen et al., "Direct Sequencing of Affinity–captured Amplified Human DNA Application to the Detection of Apolipoprotein E Polymorphism", 258:71–74 (1989).

Ware et al., "Genetic Defect Responsible for the Dysfunctional Protein: Factor IXLong Beach", Blood, 72:820–822 (1988).

Wu et al., "Allele–Specific Enzymatic Amplification of $–Globin Genomic DNA for Diagnosis of Sickle Cell Anemia", 86:2757–2760 (1989).

Wu et al., Nucleotide Sequence Analysis of DNA, *J. Molecular Biology*, 57:491–511 (1971).

Ziff et al., Determination of the Nucleotide Sequence of a Fragment of Bacteriophage ΨX 174 DNA, 241:34–37 (1973).

Robertson, et al., Isolation and Sequence Analysis of a Ribosome protected Fragment from Bacteriophage ΨX 174 DNA, 241:38–40 (1973).

Sanger, et al., Use of DNA Polymerase I Primed by a Synthetic Oligonucleotide to Determine a Nucleotide Sequence in Phage f1 DNA, *Proc. Nat. Acad. Sci. USA*, vol. 70, No. 4 1209–1213 (1973).

Maxam et al., A new method for sequencing DNA, *Proc. Natl. Acad. Sci. USA*, 74:560–564 (1977).

Tabor et al., Effect of manganese ions on the incorporation of dideoxynucleotides by bacteriphage T7 DNA polymerase and *Escherichia coli* DNA polymerase I, *Proc. Natl. Acad. Sci.*, 86:4076–4080 (1989).

Kornher et al., Mutation detection using nucleotide analogs that alter electrophoretic mobility, *Nucleic Acids Research*, 17:7779–7784 (1989).

Sokolov, Primer extenstion technique for the detection of single nucleotide in genomic DNA, *Nucleic Acids Research*, 18:3671 (1989).

Prezant et al., Trapped–Oligonucleotide Nucleotide Incorporation (TONI) Assay, a Simple Method for Screening Point Mutations, *Human Mutation*, 1:159–164 (1992).

*Anderson et al., "Sequence and Organization of the Human Mitochondrial Genome," *Nature* 290: 457–465 (1981).

*Baer et al., "DNA Sequence and Expression of the B95–8 Epstein–Barr Virus Genome," *Nature* 310: 207–211 (1984).

*Brownlee et al., "The sequence of 5s Ribosomal Ribonucleic Acid," *J. Mol. Biol.* 34:379–412 (1968).

*Gingeras, "Nucleotide Sequences from the Adenovirus–2 Genome," *J. Biol. Chem.* 257: 13475–13491 (1982).

*Huang et al., "2–(2'–Phosphoryloxyphenyl)–4(3H)–Quinazolinone Derivatives as Fluorogenic Precipitating Substrates on Phosphates," *Anal. Biochem.* 207: 32–39 (1992).

*Huang et al., "A Novel Fluorogenic Substrate for Detecting Alkaline Phosphate Activity in Situ," *J. Histochem. Cytochem.* 41: 313–317 (1993).

*Kuppuswamy, et al. "Single Nucleotide Primer Extension to Detect Genetic Diseases: Experimental Application to Hemophilia B (Factor IX) and Cystic Fibrosis Genes," *Proc. Natl Acad. Sci. USA* 88: 1143–1174 (1991).

*Nikiforov et al, "Genetic Bit Analysis: A Solid Phase Method for Typing Single Nucleotide Polymorphisms," *Nucl. Acids Res.* 22:4167–4175 (1994).

*Nikiforov et al., "The Use of Phosphorothioate Primers and Exonuclease Hydrolysis for the Preparation of Single–Stranded PCR Products and Their Detection by Solid–Phase Hybridization," *PCR Methods and Apps.* 3: 285–291 (1994).

*Nyren et al., "Solid Phase DNA Minisequencing by an Enzymatic Luminometric Inorganic Pyrophosphate Detection Assay," *Anal. Biochem.* 208: 171–175 (1993).

*Prober et al., "A System for Rapid DNA Sequencing with Fluorescent Chain–Terminating Dideoxynucleotides," *Science* 238: 336–341 (1987).

*Sanger et al., "Nucleotide Sequence of Bacteriophage λ DNA," *J. Mol. Biol.* 162: 729–773 (1982).

*Sanger et al., "A Rapid Method for Determining Sequences in DNA by Primed Synthesis with DNA Polymerase," *J. Mol. Biol.* 94: 441–448 (1975).

*Sanger, "A Two–Dimensional Fractionation Procedure for Radioactive Nucleotides," *J. Mol. Biol.* 13: 373–398 (1965).

*Shumaker et al., "Mutation Detection by Solid Phase Primer Extension", *Human Mutation* 7(4), 346–354 (1996).

*Staden, "The Current Status and Portability of Our Sequence Handling Software," *Nucl. Acids Res.* 14: 217–231 (1986).

*Syvanen et al., "Identification of Individuals by Analysis of Biallelic DNA Markers, Using PCR and Solid–Phase Minisequencing," *Amer. J. Hum. Genet.* 52: 46–59 (1993).

*Syvanen et al., "A Primer–Guided Nucleotide Incorporation Assay in the Genotyping of Apolipoprotein E," *Genomics* 8: 684–692 (1990).

*Ugozzoli et al., "Detection of Specific Alleles by Using Allele–Specific Primer Extension Followed by Capture on Solid Support," *GATA* 9: 107–112 (1992).

GBA TYPING RESULTS USING SYNTHETIC TEMPLATES ON GLASS SLIDES

METHOD FOR ANALYZING THE NUCLEOTIDE SEQUENCE OF A POLYNUCLEOTIDE BY OLIGONUCLEOTIDE EXTENSION ON AN ARRAY

CROSS-REFERENCE TO RELATED APPLICATIONS

This application is a continuation of U.S. application Ser. No. 08/616,906, filed Mar. 19, 1996, abandoned which is herein incorporated by reference.

FIELD OF THE INVENTION

The present invention relates to nucleic acid chemistry, and more specifically to a method for determining the nucleotide sequence of a polynucleotide. The invention further relates to apparatus and kits that embody or employ such a method.

BACKGROUND OF THE INVENTION

The determination of the nucleotide sequence of a polynucleotide has substantial utility in medicine, forensics, biomedical research, and in the determination of paternity and identity. Several methods for determining the nucleotide sequence of a polynucleotide have been identified.

I. Nucleic Acid Sequencing

Initial attempts to determine the sequence of a DNA molecule were extensions of techniques which had been initially developed to permit the sequencing of RNA molecules (Sanger, F., *J. Mol. Biol.* 13:373 (1965); Brownlee, G. G. et al., *J. Mol. Biol.* 34:379 (1968)). Such methods involved the specific cleavage of DNA into smaller fragments by (1) enzymatic digestion (Robertson, H. D. et al, *Nature New Biol.* 241:38 (1973); Ziff, E. B. et al., *Nature New Biol.* 241:34 (1973)); (2) nearest neighbor analysis (Wu, R., et al., *J. Mol. Biol.* 57:491 (1971)), and (3) the "Wanderings Spot" method (Sanger, F., *Proc. Natl. Acad. Sci.* (*U.S.A.*) 70:1209 (1973)).

The most commonly used methods of nucleic acid sequencing are the "dideoxy-mediated chain termination method," also known as the "Sanger Method"(Sanger, F., et al., *J. Molec. Biol.* 94:441 (1975); Prober, J. et al. Science 238:336–340 (1987)) and the "chemical degradation method," "also known as the "Maxam-Gilbert method" (Maxam, A. M., et al., *Proc. Natl. Acad. Sci.* (U.S.A.) 74:560 (1977), both references herein incorporated by reference).

A. Dideoxy-Mediated Chain Termination Method of DNA Sequencing

In the dideoxy-mediated or "Sanger" chain termination method of DNA sequencing, the sequence of a DNA molecule is obtained through the extension of an oligonucleotide primer which is hybridized to the nucleic acid molecule being sequenced. In brief, four separate primer extension reactions are conducted. In each reaction, a DNA polymerase is added along with the four nucleotide triphosphates needed to polymerize DNA. Each of the reactions is carried out in the additional presence of a 2',3' dideoxy derivative of the A, T, C, or G nucleoside triphosphates. Such derivatives differ from conventional nucleotide triphosphates in that they lack a hydroxyl residue at the 3' position of deoxyribose. Thus, although they can be incorporated by a DNA polymerase into the newly synthesized primer extension, the absence of the 3' hydroxyl group causes them to be incapable of forming a phosphodiester bond with a succeeding nucleotide triphosphate. Thus, the incorporation of a dideoxy derivative results in the termination of the extension reaction. Since the dideoxy derivatives are present in lower concentrations than their corresponding, conventional nucleotide triphosphate analogs, the net result of each of the four reactions is to produce a set of nested oligonucleotides each of which is terminated by the particular dideoxy derivative used in the reaction. By subjecting the reaction products of each of the extension reactions to electrophoresis, it is possible to obtain a series of four "ladders." Since the position of each "rung" of the ladder is determined by the size of the molecule, and since such size is determined by the incorporation of the dideoxy derivative, the appearance and location of a particular "rung" can be readily translated into the sequence of the extended primer. Thus, through an electrophoretic analysis, the sequence of the extended primer can be determined.

One deficiency of the dideoxy-mediated sequencing method is the need to optimize the ratio of dideoxy nucleoside triphosphates to conventional nucleoside triphosphates in the chain-extension/chain-termination reactions. Such adjustments are needed in order to maximize the amount of information which can be obtained from each primer. Additionally, the efficiency of dideoxy nucleotide incorporation in a particular target molecule is partially dependent upon the primary and secondary structures of the target.

The dideoxy-mediated method thus requires single-stranded templates, specific oligonucleotide primers, and high quality preparations of a DNA polymerase (typically the Klenow fragment of *E. coli* DNA polymerase I). Initially, these requirements delayed the wide spread use of the method. However, with the ready availability of synthetic primers, and the availability of bacteriophage M13 and phagemid vectors (Maniatis, T., et al., *Molecular Cloning, a Laboratory Manual. 2nd Edition* Cold Spring Harbor Press, Cold Spring Harbor, N.Y. (1989), herein incorporated by reference), the dideoxy-mediated chain termination method is now extensively employed.

B. The Maxam-Gilbert Method Of DNA Sequencing

The Maxam-Gilbert method of DNA sequencing is a degradative method. In this procedure, a fragment of DNA is labeled at one end and partially cleaved in four separate chemical reactions, each of which is specific for cleaving the DNA molecule at a particular base (G or C) at a particular type of base (A/G, C/T, or A>C). As in the above-described dideoxy method, the effect of such reactions is to create a set of nested molecules whose lengths are determined by the locations of a particular base along the length of the DNA molecule being sequenced. The nested reaction products are then resolved by electrophoresis, and the end-labeled molecules are detected, typically by autoradiography when a $^{32}P$ label is employed. Four single lanes are typically required in order to determine the sequence.

The Maxam-Gilbert method thus uses simple chemical reagents which are readily available. Nevertheless, the dideoxy-mediated method has several advantages over the Maxam-Gilbert method. The Maxam-Gilbert method is extremely laborious and requires meticulous experimental technique. In contrast, the Sanger method may be employed on larger nucleic acid molecules.

Significantly, in the Maxam-Gilbert method the sequence is obtained from the original DNA molecule, and not from an enzymatic copy. For this reason, the method can be used to sequence synthetic oligonucleotides, and to analyze DNA modifications such as methylation, etc. It can also be used to study both DNA secondary structure and protein-DNA interactions. Indeed, it has been readily employed in the identification of the binding sites of DNA binding proteins.

Methods for sequencing DNA using either the dideoxy-mediated method or the Maxam-Gilbert method are widely known to those of ordinary skill in the art. Such methods are, for example, disclosed in Maniatis, T., et al., *Molecular Cloning. a Laboratory Manual. 2nd Edition* Cold Spring Harbor Press, Cold Spring Harbor, N.Y. (1989), and in Zyskind, J. W., et al., *Recombinant DNA Laboratory Manual* Academic Press. Inc., New York (1988), both herein incorporated by reference.

Both the dideoxy-mediated method and the Maxam-Gilbert method of DNA sequencing require the prior isolation of the DNA molecule which is to be sequenced. The sequence information is obtained by subjecting the reaction products to electrophoretic analysis (typically using polyacrylamide gels). Thus, a sample is applied to a lane of a gel, and the various species of nested fragments are separated from one another by their migration velocity through the gel. The number of nested fragments which can be separated in a single lane is approximately 200–300 regardless of whether the Sanger or the Maxam-Gilbert method is used. Those of great skill in the art can separate up to 600 fragments in a single lane. Thus, in order to sequence large DNA molecules, it is necessary to fragment the molecule, and to sequence the fragments in separate lanes of the sequencing gel. The sequence of the entire molecule is obtained by orienting and ordering the sequence data obtained from each fragment.

Two approaches have been employed by those of skill in this art to accomplish this goal. In a random or shotgun sequencing approach, sequence data is collected by subcloning fragments of the target DNA molecule. No attempt is initially made to determine the linear orientation or order of the subclones with respect to the intact target DNA molecule. Instead, the accumulated data are stored and ultimately arranged into order by a computer (Staden, R., *Nucleic Acids Res.* 14:217 (1986); Anderson, S. et al, *Nature* 290:457 (1981); Gingeras, T. R., *J. Biol. Chem.* 257:13475 (1982); Sanger, F. et al, *J. Mol. Biol.* 162:729 (1982), and Baer, R. et al, *Nature* 310:207 (1984)). As will be appreciated, such random shotgun approaches often result in the multiple sequencing of the same oligonucleotide fragment, and thus are often inefficient in terms of time and materials.

In contrast, directed approaches have been employed in which sequences of the target DNA are obtained in a systematic fashion. For example, the target DNA molecule may be ordered by restriction mapping using the methods described above, and the discrete restriction fragments sequenced. Alternatively, the target molecule may be sequenced by sequencing nested sets of deletions which begin at one of its ends. The use of such nested fragments progressively brings more and more remote regions of the target DNA into range for sequencing. Lastly, sequence information obtained from a particular target molecule can be used to prepare a primer which can then be used in a subsequent sequencing reaction in order to obtain additional sequence information. As will be perceived, a directed sequence analysis of a target DNA molecule often requires substantial a priori information regarding the sequence. Moreover, for large target molecules (of sizes on the order of kilobases) such as would be encountered in the sequencing of eukaryotic (and in particular, mammalian) chromosomes, directional sequencing is quite arduous.

II. Microsequencing and GBA™ Genetic Analysis

In contrast to the "Sanger Method" and the "Maxam-Gilbert method," which identify the sequence of all of the nucleotides of a target polynucleotide, "microsequencing" methods determine the identity of only a single nucleotide at a "predetermined" site. Such methods have particular utility in determining the presence and identity of polymorphisms in a target polynucleotide.

The GBA™ Genetic Bit Analysis method disclosed by Goelet, P. et al. (WO 92/15712, herein incorporated by reference) is a particularly useful microsequencing method. In GBA™, the nucleotide sequence information surrounding a predetermined site of interrogation is used to design an oligonucleotide primer that is complementary to the region immediately adjacent to, but not including, the predetermined site. The target DNA template is selected from the biological sample and hybridized to the interrogating primer. This primer is extended by a single labeled dideoxynucleotide using DNA polymerase in the presence of at least two, and most preferably all four chain terminating nucleoside triphosphate precursors.

Additional, primer-guided, nucleotide incorporation procedures for assaying polymorphic sites in DNA have also been described (Komher, J. S. et al, *Nucl. Acids. Res.* 17:7779–7784 (1989); Sokolov, B. P., *Nucl. Acids Res.* 18:3671 (1990); Syvänen, A. -C., et al., *Genomics* 8:684–692 (1990); Kuppuswamy, M. N. et al., *Proc. Natl. Acad. Sci. (U.S.A.)* 88:1143–1147 (1991); Prezant, T. R. et al, *Hum. Mutat.* 1:159–164 (1992); Ugozzoli, L. et al., *GATA* 9:107–112 (1992); Nyren, P. et al., *Anal. Biochem.* 208:171–175 (1993); and Wallace, WO89/10414). These methods differ from Genetic Bit™ Analysis in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvänen, A. -C., et al. *Amer. J. Hum. Genet.* 52:46–59 (1993)). Such a range of locus-specific signals could be more complex to interpret, especially for heterozygotes, compared to the simple, ternary (2:0, 1:1, or 0:2) class of signals, produced by the GBA™ method. In addition, for some loci, incorporation of an incorrect deoxynucleotide can occur even in the presence of the correct dideoxynucleotide (Komher, J. S. et al., *Nucl. Acids. Res.* 17:7779–7784 (1989)). Such deoxynucleotide misincorporation events may be due to the Km of the DNA polymerase for the mispaired deoxy- substrate being comparable, in some sequence contexts, to the relatively poor Km of even a correctly base paired dideoxy- substrate (Kornberg, A., et al., In: DNA Replication, Second Edition (1992), W. H. Freeman and Company, New York; Tabor, S. et al., *Proc. Natl. Acad. Sci. (U.S.A.)* 86:4076–4080 (1989)). This effect would contribute to the background noise in the polymorphic site interrogation.

Mundy, C.R. (U.S. Pat. No. 4,656,127) discusses alternative microsequencing methods for determining the identity of the nucleotide present at a particular polymorphic site. Mundy's methods employ a specialized exonuclease-resistant nucleotide derivative. A primer complementary to the allelic sequence immediately 3'-to the polymorphic site is permitted to hybridize to a target molecule obtained from a particular animal or human. If the polymorphic site on the target molecule contains a nucleotide that is complementary to the particular exonucleotide-resistant nucleotide derivative present, then that derivative will be incorporated by a polymerase onto the end of the hybridized primer. Such incorporation renders the primer resistant to exonuclease, and thereby permits its detection. Since the identity of the exonucleotide-resistant derivative of the sample is known, a finding that the primer has become resistant to exonucleases reveals that the nucleotide present in the polymorphic site of the target molecule was complementary to that of the nucleotide derivative used in the reaction. The Mundy method has the advantage that it does not require the determination of large amounts of extraneous sequence data. It has the disadvantages of destroying the amplified target sequences, and unmodified primer and of being extremely sensitive to the rate of polymerase incorporation of the specific exonuclease-resistant nucleotide being used.

Cohen, D. et al (French Patent 2,650,840; PCT Appln. No. WO91/02087) discuss a solution-based method for determining the identity of the nucleotide of a polymorphic site. As in the Mundy method of U.S. Pat. No. 4,656,127, a primer is employed that is complementary to allelic sequences immediately 3'-to a polymorphic site. The method determines the identity of the nudeotide of that site using labeled dideoxynucleoside derivatives, which, if complementary to the nucleotide of the polymorphic site will become incorporated onto the terminus of the primer.

In contrast to the method of Cohen et al. (French Patent 2,650,840; PCT Appln. No. WO91/02087) the GBA™ method of Goelet, P. et al. can be conducted as a heterogeneous phase assay, in which the primer or the target molecule is immobilized to a solid phase. It is thus easier to perform, and more accurate than the method discussed by Cohen. The method of Cohen has the significant disadvantage of being a solution-based extension method that uses labeled dideoxynucleoside triphosphates. In the Cohen method, the target DNA template is usually prepared by a DNA amplification reaction, such as the PCR, that uses a high concentration of deoxynucleoside triphosphates, the natural substrates of DNA polymerases. These monomers will compete in the subsequent extension reaction with the dideoxynucleoside triphosphates. Therefore, following the PCR, an additional purification step is required to separate the DNA template from the unincorporated dNTPs. Because it is a solution-based method, the unincorporated dNTPs are difficult to remove and the method is not suited for high volume testing.

III. Sequencing via Hybridization to Ordered Oligonucleotide Arrays

In response to the difficulties encountered in employing gel electrophoresis to analyze sequences, alternative methods have been developed. Macevicz (U.S. Pat. No. 5,002, 867), for example, describes a method for determining nucleic acid sequence via hybridization with multiple mixtures of oligonucleotide probes. In accordance with such method, the sequence of a target polynucleotide is determined by permitting the target to sequentially hybridize with sets of probes having an invariant nucleotide at one position, and a variant nucleotides at other positions. The Macevicz method determines the nucleotide sequence of the target by hybridizing the target with a set of probes, and then determining the number of sites that at least one member of the set is capable of hybridizing to the target (i.e. the number of "matches" ). This procedure is repeated until each member of a sets of probes has been tested.

IV. Limitation of Conventional Methods

Several factors may limit the use of conventional methods in the analysis of the nucleotide sequence of a target molecule. Typically, each lane of a sequencing gel can resolve only about 300 different fragments. Thus, in order to determine the nucleotide sequence of a large DNA molecule, multiple sequencing gels are often needed. This, in turn, limits the amount of new sequence information which can be readily obtained per day. For a large nucleic acid molecule, a substantial number of technically demanding and time consuming steps must be performed. In particular, since the above-described techniques are capable of analyzing only one set of nested oligonucleotides per sample, the sequencing of large DNA molecules requires the use of multiple sequencing gels each having a large number of lanes. The electrophoretic analysis step in the sequencing process thus comprises a significant limitation to the amount of sequence information which can be obtained and the rate with which it can be processed.

In summary, a method which would permit accurate nucleotide sequencing without gel analysis would be highly desirable. Indeed, for the analysis of very large genomes, such as the human genome, the development of such methods may be essential.

SUMMARY OF THE INVENTION

The invention provides a solid phase sequencing method for determining the sequence of nucelic acid molecules (either DNA or RNA). In detail, the invention provides a method for determining the nucleotide sequence of a nucleic acid molecule which comprises the steps of:

(A) arraying a set of nested primer oligonucleotides onto a solid support, each array position containing a different array member having a predetermined sequence;

(B) incubating oligonucleotides of the array in the presence of a preparation of the nucleic acid molecules, a polymerase and at least one chain terminator nucleotide; wherein the incubation is under conditions sufficient to permit DNA hybridization to occur between the oligonucleotides of the incubation and the nucleic acid molecules; wherein the incubation is conducted in the substantial absence of any non-chain terminator nucleotides;

(C)(1) in the case wherein the 3' terminal nucleotide of an oligonucleotide is hybridized to the nucleic acid molecule, permitting oligonucleotides hybridized to nucleic acid molecules to be extended by polymerase-mediated incorporation of a single chain terminator nucleotide residue onto the 3' terminus of the hybridized oligonucleotide, wherein for each hybridized oligonucleotide being so extended, the incorporated nucleotide residue is complementary to the nucleotide residue immediately 5' to the nucleotide residue of the nucleic acid molecule that is hybridized with that oligonucleotide's 3' terminal nucleotide residue; then performing step (D);

(2) in the case wherein the 3' terminal nucleotide of an oligonucleotide is not hybridized to the nucleic acid molecule, either:
 (a) not permitting oligonucleotides hybridized to nucleic acid molecules to be extended by polymerase-mediated incorporation of a single chain terminator nucleotide residue onto the 3' terminus of the hybridized oligonucleotide, or
 (b) permitting the removal of any non-hybridized nucleotide residues from the 3' terminus of the hybridized oligonucleotides, so as to form a truncated primer oligonucleotide whose 3' terminus is hybridized to the nucleic acid molecule, and then permitting polymerase-mediated incorporation of a single chain terminator nucleotide residue onto the 3' terminus of the hybridized truncated oligonucleotide, wherein for each hybridized truncated oligonucleotide being so extended, the incorporated nucleotide residue is complementary to the nucleotide residue immediately 5' to the nucleotide residue of the nucleic acid molecule that is hybridized with that truncated oligonucleotide's 3' terminal nucleotide residue; then performing step (D);

(D) determining, at each array position at which an oligonucleotide has incorporated a single chain terminator nucleotide residue, the identity of the incorporated chain terminator nucleotide residue; and (E) determining the nucleotide sequence of the nucleic acid molecule from the determined identity of the incorporated nucleotide of primer oligonucleotides of the array, and known sequence of the oligonucleotide at each array position.

The invention particularly concerns embodiments in each array position contains a primer oligonucleotide that is capable of hybridizing to a region of the nucleic acid molecule, and/or wherein in step (C), at least some array positions contain nucleic acid molecules hybridized to oligonucleotides the whose 3' terminal nucleotide is not hybridized to the nucleic acid molecule, and wherein step (C)(1) is conducted for such oligonucleotides Either a Thermosequenase class polymerase or a Klenow class polymerase may be employed in the method.

The invention particularly includes the embodiments in which the array is a random oligonucleotide array, and in which the array is a nested oligonucleotide array (especially one containing oligonucleotide members having all possible permutations of nucleotides over a region of from 1 to 20 bases.

The invention is particularly adapted or conducting the method in the presence of at least four chain terminator nucleotide species, at least one of which is labeled, and more preferably wherein all of the chain terminator nucleotide species are labeled, and wherein the label of any such species can be distinguished from the label of any other species present.

The invention particularly provides a method of sequence determination for genomic DNA of a human or non-human mammal, and is especially adapted for use in determining the sequence of DNA suspected to contain a genetic variation associated with a disease (e.g., cancer or cystic fibrosis), and in which the method is employed to determine whether the DNA contains the variation.

In a preferred embodiment of the method, the oligonucleotides are immobilized onto the solid support, such as plastic or glass).

The invention also provides a kit for determining the sequence of a nucleic acid molecule which comprises a solid support containing an array of spaced apart receptacles for oligonucleotides, each receptacle containing a different primer oligonucleotide. The kit may additionally contain at least four chain terminator nucleotide species, at least one of which is labeled. A highly preferred kit contains at least four chain terminator nucleotide species, wherein all of the chain terminator nucleotide species are labeled, and wherein the label of any such species can be distinguished from the label of any other species present.

The kit is particularly suited for determining the nucleotide sequence of DNA suspected to contain a genetic variation associated with a disease, and to provide a determination of nucleotide sequence sufficient to determine whether the DNA contains the variation.

DESCRIPTION OF THE PREFERRED EMBODIMENTS

Figure 1:
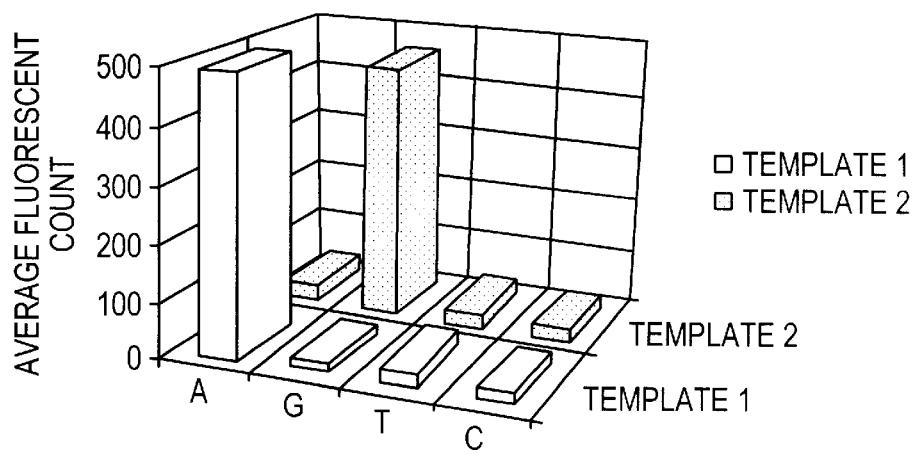
FIG. 1 shows the result of a nested GBA™ (N-GBA™) experiment.

The present invention provides a method of sequencing which provides the advantages of micro- and nano-sequencing and has the ability to sequence polynucleotide regions. In brief, the method employs ordered arrays of linear primers that are capable of hybridizing to a target molecule and reporting the identity of the single nucleotide that is present in the hybridized molecule immediately 5' to the 3' terminus of the primer. By employing a suitable array of such primers, the invention permits one to ascertain he complete nucleotide sequence of a target polynucleotide. There are thus two central aspects to the present invention: the method of sequence analysis, and the nature of the primer array.

I. GBA™ Sequence Analysis

The most preferred method of the present invention employs a modification of the GBA™ method of analyzing a predetermined site as the means for accomplishing sequence analysis. The GBA™ method can be conducted in a variety of ways. In particular, such interrogation can be accomplished via a polymerase-mediated analysis or by a ligase-mediated analysis.

A. Polymerase-Mediated Analysis

The polymerase-mediated analysis is more fully described by Goelet, P. et al. (PCT Application WO92/15712, herein incorporated by reference). In this assay, a purified oligonucleotide having a defined sequence (complementary to an immediate proximal or distal sequence of a polymorphism) is bound to a solid support, especially a microtiter dish. A sample, suspected to contain the target molecule, or an amplification product thereof, is placed in contact with the support, and any target molecules present are permitted to hybridize to the bound oligonucleotide.

In one preferred embodiment, an oligonucleotide having a sequence that is complementary to an immediately distal sequence of a polymorphism is prepared using the above-described methods (and preferably that of Nikiforov, T. (U.S. patent application Ser. No. 08/005,061, herein incorporated by reference). The terminus of the oligonucleotide is attached to the solid support, as described, for example by Goelet, P. et al. (PCT Application WO 92/15712), such that the 3'-end of the oligonucleotide can serve as a substrate for primer extension.

The immobilized primer is then incubated in the presence of a DNA molecule (preferably a genomic DNA molecule) having a single nucleotide polymorphism whose immediately 3'-distal sequence is complementary to that of the immobilized primer. Preferably, such incubation occurs in the complete absence of any dNTP (i.e. dATP, dCTP, dGTP, or dTTP), but only in the presence of one or more chain terminating nucleotide triphosphate derivatives (such as a dideoxy derivative), and under conditions sufficient to permit the incorporation of such a derivative on to the 3'-terminus of the primer. As will be appreciated, where the polymorphic site is such that only two or three alleles exist (such that only two or three species of dNTPs, respectively, could be incorporated into the primer extension product), the presence of unusable nucleotide triphosphate(s) in the reaction is immaterial. In consequence of the incubation, and the use of only chain terminating nucleotide derivatives, a single dideoxynucleotide is added to the 3'-terminus of the primer. The identity of that added nucleotide is determined by, and is complementary to, the nucleotide of the polymorphic site of the polymorphism.

In this embodiment, the nucleotide of the polymorphic site is thus determined by assaying which of the set of labeled nucleotides has been incorporated onto the 3'-terminus of the bound oligonucleotide by a primer-dependent polymerase. Most preferably, where multiple dideoxynucleotide derivatives are simultaneously employed, different labels will be used to permit the differential determination of the identity of the incorporated dideoxynucleotide derivative.

B. Polymerase/Ligase-Mediated Analysis

In an alternative embodiment, the identity of the nucleotide of the polymorphic site is determined using a polymerase/ligase-mediated process. As in the above embodiment, an oligonucleotide primer is employed, that is complementary to the immediately 3'-distal invariant sequence of the polynucleotide being analyzed. A second oligonucleotide, is tethered to the solid phase via its 3'-end. The sequence of this oligonucleotide is complementary to the 5'-proximal sequence of the predetermined site being analyzed, but is incapable of hybridizing to the oligonucleotide primer.

These oligonucleotides are incubated in the presence of DNA containing the single nucleotide polymorphism that is to be analyzed, and at least one 2', 5'-deoxynucleotide triphosphate. The incubation reaction further includes a DNA polymerase and a DNA ligase.

The tethered and soluble oligonucleotides are thus capable of hybridizing to the same strand of the single nucleotide polymorphism under analysis. The sequence considerations cause the two oligonucleotides to hybridize to the proximal and distal sequences of the polynucleotide site that flank the predetermined site; the hybridized oligonucleotides are thus separated by a "gap" of a single nucleotide at the precise position of the predetermined site.

The presence of a polymerase and a deoxynucleotide complementary to the nucleotide of the gap permits ligation of the primer extended with the complementary deoxynucleotide to the immobilized oligonucleotide complementary to the distal sequence, a deoxynucleotide triphosphate that is complementary to the nucleotide of the polymorphic site permits the creation of a ligatable substrate. The ligation reaction immobilizes the deoxynucleotide and the previously soluble primer oligonucleotide to the solid support.

The identity of the polymorphic site that was opposite the "gap" can then be determined by any of several means. In a preferred embodiment, the deoxynucleotide of the reaction is labeled, and its detection thus reveals the identity of the complementary nucleotide of the predetermined site. Several different deoxynucleotides may (and preferably will) be present, each differentially labeled. Alternatively, separate reactions can be conducted, each with a different deoxynucleotide. In an alternative sub-embodiment, the deoxynucleotides are unlabeled and a labeled dideoxynucleotide is employed, and the second, soluble oligonucleotide is labeled. Separate reactions are conducted, each using a different unlabeled dideoxynucleotide. The reaction that contains the complementary nucleotide permits the ligatable substrate to form, and is detected by detecting the immobilization of the previously soluble oligonucleotide.

C. Signal-Amplification

The sensitivity of nucleic acid hybridization detection assays may be increased by altering the manner in which detection is reported or signaled to the observer. Thus, for example, assay sensitivity can be increased through the use of detectably labeled reagents. A wide variety of such signal amplification methods have been designed for this purpose. Kourilsky et al. (U.S. Pat. No. 4,581,333) describe the use of enzyme labels to increase sensitivity in a detection assay. Fluorescent labels (Prober, J. et al. Science 238:336–340 (1987); Albarella et al., EP 144914), chemical labels (Sheldon III et al., U.S. Pat. No. 4,582,789; Albarella et al., U.S. Pat. No. 4,563,417), modified bases (Miyoshi et al., EP 119448), etc. have also been used in an effort to improve the efficiency with which hybridization can be observed.

It is preferable to employ fluorescent, and more preferably chromogenic (especially enzyme) labels, such that the identity of the incorporated nucleotide can be determined in an automated, or semi-automated manner using a spectrophotometer.

D. Use of GBA™ Analysis in the Methods of the Present Invention

GBA™ was developed as a solid-phase single nucleotide polymorphism genotyping method based on single-base extension of an interrogation primer across a target base of interest. In contrast to gel-based testing, a solid-phase array can be manufactured in a standardized way with quality control, thereby ensuring that variation in performance of the test is more a factor of input DNA quality and less of operator expertise. The present invention extends this method to a N-GBA™ format, with the complementary interrogation primers nested at one (or more) base intervals across the target sequence, and thus enables detailed sequence analysis of a complex target DNA sequence. While GBA™ is well suited to single-base interrogations, the N-GBA™ method of the present invention is ideally suited to analysis of intermediate length (10–100 base) DNA target sequences. Application of the N-GBA™ method in a Sequence Confirmation/composition ANalysis (SCAN™) - chip prototype (a miniaturized array of interrogation primers on a glass slide) is the most preferred embodiment of the method, and permits standardized (through manufacture of the oligonucleotide interrogation primer arrays), lower cost (through miniaturization of the test) and accurate (through use of the GBA™ biochemistry) scanning for p53 mutations.

The solid-phase format of the present invention also provides advantages in processing, since reagents can be added by hand at small scales, or by robots on a larger scale, without changes to the test. The size of the arrays can be controlled as well, so that the advantages of miniaturization can be realized: thus a 30 μl PCR reaction can be hybridized simultaneously to hundreds or thousands of oligonucleotides in an array only a few millimeters in diameter. In this way, processing can be performed at a "macro" scale, using standard pipetters, and information extracted at a "micro" or "nano" scale using fluorescent imaging. These advantages provide a lower cost test having much more reproducible performance. Unlike methods that rely on hybridization as the method of analysis, the methods of the present invention exploit the use of primer extension biochemistry for nucleotide-by-nucleotide analysis and its application to a solid-phase oligonucleotide array format. The addition of primer extension to solid-phase analysis adds significant increases in test accuracy and differential sensitivity over hybridization-based approaches while exploiting the advantages of solid-phase-based testing over gel-based tests.

This strategy of nesting the GBA™ across a region of interest eliminates any need to "expect" (i.e., guess in advance) a particular mutation. Nesting eliminates any need to limit analysis to a specific nucleotide. Current GBA™ detection technology is a "two-result" system (distinguishing wild-type from mutant). An additional innovation of the preferred embodiments of the present invention involves the use of a "four-result" system, which, by parallel detection of all four possible DNA bases for each site in the sequence, provides enhanced accuracy. With this innovation, the change of any nucleotide in the target region to any other possible base will be detectable in a base-specific fashion, thus any mutation in a proposed target hot-spot will be identifiable, including novel mutations.

In one embodiment, this is accomplished by separating the arrays into four identical array spots to which PCR or other amplified product can hybridize equally. The GBA™ extension is thus preferably divided into four reaction mixes, each containing a different haptenated dideoxynucleotide triphosphate (ddNTP). The four spots represent the four possible bases: G, A, T and C, and incorporation of each possible base can be evaluated for each oligonucleotide in the array and from this the sequence composition of the target fragment deduced. The SCAN™ -chip format, utilizing N-GBA™ biochemistry, will thus enable: highly accurate mutation detection due to the sensitivity of primer extension to hybridization mismatch at the 3' (extended) end of the interrogation primer; increased informativeness since the mutation is detected in a highly localized fashion; relatively standardizable and simple testing due to the SCAN™ format; and cost-effectiveness due to miniaturization of the arrays.

In accordance with the methods of the present invention, the target polynucleotide (i.e., the nucleic acid molecule that is to be sequenced) is provided to each array position of a spacially separated array of oligonucleotide primers in single-stranded form, under conditions sufficient to permit hybridization to occur. As used herein, an array of oligonucleotides is said to be "spacially separated" if an oligonudeotide of one sequence is separated from an oligonucleotide of another sequence. In the microminiaturized method described below, each oligonucleotide species of the array is provided to a separate microtiter well. In contrast, in the nanominiaturiuzed method, each oligonucleotide species of the array is provided to a distinct region of a surface, such as a glass slide, etc. As used herein, the term "array" is intended to define a two dimensional or three dimensional matrix having a definition of X,Y or X,Y,Z, such that, for example, at array position 1,1 a particular oligonucleotide is found; an oligonucleotide of different sequence is found at array position 1,2 or 2,1, etc. For each array, the oligonucleotide found at each array position is defined and known in advance of any reaction.

The sequence of each oligonucleotide of each array position is selected such that it will be shorter in length than the target polynucleotide being sequenced. Most preferably, such nucleotides will be less that 30 bases in length, and most preferably less than 10 bases. Oligonucleotides of 5 bases in length are preferred. As such, if an oligonucleotide of N residues hybridizes to the target polynucleotide, its 3' terminus (residue N) will hybridize to a nucleotide of the target polynucleotide, and can be extended via a template-dependent polymerization reaction to incorporate an "interrogation nucleotide" as residue N+1 of that oligonucleotide. The identity of the "interrogation nucleotide" is dependent upon (and is complementary to) the nucleotide species of the target polynucleotide that is present immediately 5' adjacent to the nucleotide that hybridizes to the 3' terminus of the oligonucleotide, prior to the polymerization reaction.

Each array position additionally contains more than one different nucleotide specie, such that nucleotide species are present that are complementary to at least two, and in the most preferred embodiment, all four of the nucleotide species of DNA (i.e., adenosine, cytosine, thymidine and guanosine, designated A, C, T and G, respectively). The nucleotide species present are "chain terminator" nucleotides. Although such nucleotide species can be incorporated onto the 3' terminus of an oligonucleotide by a DNA polymerase, the resultant extended oligonucleotide cannot be further extended by a polymerase, even in the presence of non-terminator nucleotides. The most preferred chain terminator nucleotide species of the present invention are 2'-deoxynucleoside 5'-triphosphates. The chain terminator nucleotide species are detectably labeled, such that an extension reaction that results in the incorporation of a nucleotide complementary to one of the nucleotide species of DNA can be distinguished from an extension reaction that results in the incorporation of a nucleotide complementary to a different nucleotide species of DNA. Any of the conventionally used radioisotopic, enzymatic, fluorescent or chemiluminescent labels may be used in accordance with the methods of the present invention. In lieu of such labels, haptenic labels, such as biotin or other labels such as ligands, antigens, etc. may be used. Suitable labels are disclosed, for example, by Kourilsky et al. (U.S. Pat. No. 4,581,333), Prober et al. (Science 238:336–340 (1987)); Albarella et al. (EP 144914), Sheldon m et al. (U.S. Pat. No. 4,582,789), Albarella et al. (U.S. Pat. No. 4,563,417), and Miyoshi et al. (EP 119448).

It is however, preferred to employ the enzyme-mediated fluorescence precipitation method (Huang, Z. et al., *Anal Biochem* 207:32–39 (1992), herein incorporated by reference). In this method of detection, a fluorogenic signal is determined by precipitation at a localized reaction site. This novel detection chemistry actually combines the powers of enzymatic amplification, rapid in situ product precipitation, high contrast of fluorescence signal over (glass) background, and quantitation of fluorescent signal. The method thus provides greater sensitivity than direct fluorescence detection and is operationally compatible with a high density oligonucleotide glass array format.

A polymerase, and suitable salts and buffers are also provided to each array position. The reaction conditions are maintained such that the oligonucleotides stably and specifically hybridize to the target polynucleotide, and so that the 3'-terminus of the oligonucleotides are extended by addition of single chain terminator nucleotide (i.e., the interrogation nucleotide). As used herein, "stable" hybridization refers to a hybridization that has a Tm greater than the temperature under which the interrogation assay is to be run (generally 20–40° C.). The term "specific" hybridization denotes that the length and/or sequence complexity of the oligonucleotides involved in the hybridization are sufficient to preclude non-desired spurious hybridization (as might occur, for example, between sequences that are only partially complementary). The hybridization is usually carried out for 15 to 30 minutes at room temperature in a solution containing 1.5 M NaCl and 10 mM EDTA. Other hybridization conditions can alternatively be used. The sequence of the immobilized oligonucleotide is selected such that it will hybridize to the invariant sequence that flanks the polymorphic site of the polymorphism that is to be interrogated.

If the ligase/polymerase mediated GBA™ interrogation method is to be employed, the methods of Nikiforov et al. (U.S. patent application Ser. No.: 08/192,631, abandoned herein incorporated by reference) are preferably employed.

Most preferably, the oligonucleotides present at each array position are immobilized to the solid surface of the array support. Such a support may be a microtiter dish, test tube array, etched glass surface, etc.

II. Nature of the Oligonucleotide Array

The nature of the oligonucleotide array may vary depending upon the amount of prior sequence information available concerning the target molecule. In one embodiment of the invention, the array is "non-random." As used herein, a "non-random" oligonucleotide array is a set of oligonucleotides whose members do not contain all possible permutations of nucleotides. A non-random array is preferably employed when determining the nucleotide sequence of a polynucleotide for which some a priori sequence information is available. Thus, for example, non-random arrays would be employed in sequencing those genes of a patient for which the sequence of "normal" alleles had been previously determined. In contrast, a "random" array of oligonucleotides is a set of oligonucleotides whose members do contain all possible permutations of nucleotides. A random array is preferably employed when determining the nucleotide sequence of a polynucleotide for which little or no a priori sequence information is available.

Primer design is preferably facilitated through the use of the GBA™ Primer 1.0 program (Molecular Tool, Inc.) Primer stability (measured in -kcal/mol) and potential sequence-based sources of noise are evaluated by this program. A number of sequence-based features can lead to GBA™ noise for a particular target site. The most common source of noise is template-independent noise (TIN) and results from self-priming by the GBA™ primer. To eliminate TIN, GBA™ primers may be modified by a base substitution with C3 linker or by shortening the primer at the 5' end without sacrificing hybridization stability of the template strand. In the N-GBA™ system, a set of GBA™ primers which complement the target sequence and are staggered by one base will be designed according to the standard GBA™ primer design strategies described above. An example of N-GBA™ primer design was shown in a model study described in the relevant experience section.

A. Non-Random Nested Arrays

In circumstances in which the part of the sequence of the target molecule (or of a normal or reference sequence) has been previously determined, the oligonucleotide array can comprise a set of non-random nested oligonucleotides.

In the simplest embodiment, the nested primer array will contain all possible divergent sequences over the region whose sequence is to be determined. The maximum number of primers needed to determine the sequence of N nucleotides is given by the equation:

$$\sum_{1}^{N} 4^{N-1}$$

As such, the maximum number of sequences needed to obtain the sequence of even a relatively small region rises rapidly when non-random arrays are employed, the method is not preferred when more extensive sequencing is desired.

For example, a maximum of 349,525 primers would be needed to obtain 10 nucleotides of sequence information by this method. Hence, for obtaining such (or even more extensive) sequence information, the random array method described below is preferably employed.

Thus, to sequence four nucleotides in the simplest embodiment, a set of (1+4+16+64=) 85 primers would be needed. This aspect of the invention is illustrated in Table 1, which shows the sequences of four arrays of nested non-random 25-mer oligonucleotides ("oligos"), comprising all possible permutations of sequence on the final 3 nucleotides. The extent of nesting shown in Table 1 is one nucleotide, however, the array oligonucleotides can be nested by more than one nucleotide if desired. By using each oligonucleotide of a set as a GBA™ primer in a GBA™ reaction (either in the presence of three unlabeled terminator nucleotides and one labeled chain terminator nucleotide or in the presence of four differentially labeled chain terminator nucleotides), it is possible to determine the nucleotide sequence of the particular nucleic acid molecule of a sample that is complementary to the set of primers.

In some circumstances fewer primers may be employed. For example, if it were known that only one of two nucleotide candidates were possible at position 27 (e.g., either A or C, but not T or G), only (1+2+8=) 11 primers would be needed sequence the three nucleotide positions of any particular target molecule.

TABLE 1

| SEQ ID NO NO | Nucleotide Sequence of Positions 1–25 | Position Sequenced |
| --- | --- | --- |
| 1 | CTTGTGCTGACTTACCAGATGGGAC | 26 |
| 2 | TTGTGCTGACTTACCAGATGGGACA | 27 |
| 3 | TTGTGCTGACTTACCAGATGGGACC | |
| 4 | TTGTGCTGACTTACCAGATGGGACT | |
| 5 | TTGTGCTGACTTACCAGATGGGACG | |
| 6 | TGTGCTGACTTACCAGATGGGACAA | 28 |
| 7 | TGTGCTGACTTACCAGATGGGACAC | |
| 8 | TGTGCTGACTTACCAGATGGGACAT | |
| 9 | TGTGCTGACTTACCAGATGGGACAG | |
| 10 | TGTGCTGACTTACCAGATGGGACCA | |
| 11 | TGTGCTGACTTACCAGATGGGACCC | |
| 12 | TGTGCTGACTTACCAGATGGGACCT | |
| 13 | TGTGCTGACTTACCAGATGGGACCG | |
| 14 | TGTGCTGACTTACCAGATGGGACTA | |
| 15 | TGTGCTGACTTACCAGATGGGACTC | |
| 16 | TGTGCTGACTTACCAGATGGGACTT | |
| 17 | TGTGCTGACTTACCAGATGGGACTG | |
| 18 | TGTGCTGACTTACCAGATGGGACGA | |
| 19 | TGTGCTGACTTACCAGATGGGACGC | |
| 20 | TGTGCTGACTTACCAGATGGGACGT | |
| 21 | TGTGCTGACTTACCAGATGGGACGG | |
| 22 | GTGCTGACTTACCAGATGGGACAAA | 28 |

However, and as discussed above, the GBA™ reaction exploits the ability of the 3' terminus of the GBA™ primer to hybridize to the target molecule being interrogated. This characteristic of the present invention permits sequence determinations with far fewer primers, depending upon the class of polymerase being employed in the GBA™ reaction. In general, there are two classes of polymerases. One class, typified by the Klenow fragment of E. coli DNA polymerase I (Klenow class) possess 3' to 5' exonuclease activity, and are able to correct 3' base mismatches in the extended primer. The second class, typified by the thermostable polymerase, Thermosequenase (USB), (Thermosequenase class) do not possess 3' to 5' exonuclease activity, and are thus unable to correct 3' base mismatches in the extended primer. Polymerases of either class can be employed in accordance with the present invention. The characteristics of polymerases are shown in Table 2.

TABLE 2

| Enzyme | 3' to 5' Exonuclease Activity | Ability to Correct Mismatch | Possible Outcome (Signal:Noise) |
|---|---|---|---|
| Klenow Fragment | Strong | Strong | Low |
| Exo(−) Klenow | None | Moderate | Moderate |
| Sequenase | None | Moderate | Moderate |
| AmpliTaq | None | Weak | High |
| Bst Polymerase | None | Weak | High |
| Thermosequenase | None | Weak | High |

Since Thermosequenase class polymerases do not possess 3' to 5' exonuclease activity, unless a priori sequence information is available, it is preferable to employ each oligonucleotide in a nested set of all possible permutations. Nevertheless, in many circumstances incomplete sets of oligonucleotides may be employed in concert with Thermosequenase class polymerases. For example, if SEQ ID NO:1, SEQ ID NO:2, SEQ ID NO:6 and SEQ ID NO:22 were employed to sequence a target having a sequence other than GTTT at positions 25–28, one or more of the oligonucleotides would fail to hybridize its 3' terminus to the target, and minimal nucleotide incorporation would result. Hence a result indicating that GBA™ reactions on a particular target molecule led to the incorporation of a label for SEQ ID NO:1 and SEQ ID NO:2, but not for SEQ ID NO:6 or SEQ ID NO:22 would indicate that the nucleotides at positions 27–28 were not Ts. In one embodiment, such an observation of impaired incorporation is a useful indication that the sequence of the target molecule differs from that of the reference allele. As such, this embodiment is useful in identity and paternity analysis, and in genetic screening.

In contrast, since Klenow class polymerases can correct mismatches as well as extend primers, when such polymerases are employed in the GBA™ reaction, incorporation of label may reflect primer repair as well as primer extension. Thus, the use of Klenow class polymerases in the present invention has a salient advantage. Instead of needing to provide all permutations of the sequence to be determined, one need provide only one oligonucleotide for each position to be determined. Thus, to determine the sequence of positions 26–29 in the example shown above, one would need to provide at most 4 oligonucleotides (i.e. an oligonucleotide, such as SEQ ID NO:1 ending at position 26, an oligonucleotide, such as SEQ ID NO:2 ending at position 27, an oligonucleotide, such as SEQ ID NO:6 ending at position 28, and an oligonucleotide, such as SEQ ID NO:22 ending at position 29.

Thus, when Klenow class polymerases are employed, two possibilities exist with respect to such an array: a particular nucleotide may become labeled by extension, or it may become labeled by primer mismatch repair. In general, only a single unambiguous sequence will be obtained. For example, Table 3 gives the results that would be obtained from the use of SEQ ID NO:1, SEQ ID NO:2, SEQ ID NO:6 and SEQ ID NO:22 to evaluate a particular target molecule having the sequence CATGCG at nucleotide positions 25–30.

TABLE 3

| SEQ ID NO | Nucleotide Sequence of Positions 1–25 | Position No. of Nudeotide Sequenced by Array | Nucleotide Reported |
|---|---|---|---|
| 23 | CCGTACTCCCATCTGGTAAGTCAGCACAAG | | |
| 1 | CTTGTGCTGACTTACCAGATGGGAC | 25 | G |
| 2 | TTGTGCTGACTTACCAGATGGGACA | 25 | G |
| 6 | TGTGCTGACTTACCAGATGGGACAA | 28 | C |
| 22 | GTGCTGACTTACCAGATGGGACAAAA | 28 | C |

In the case of SEQ ID NO:1, the incorporation of G reflects the removal of the 3' terminal C residue, and the incorporation of a G (as the nucleotide complementary to the C at position 25 in the target). In the case of SEQ ID NO:2, the incorporation of G reflects the removal of the 3' terminal A and C residues, and the incorporation of a G (as the nucleotide complementary to the C at position 25 in the target). In the case of SEQ ID NO:6, the incorporation of T reflects the hybridization of the 3' terminus of the primer to the target, and the extension of the primer by one nucleotide (C, the nucleotide complementary to the C at position 25 in the target. In the case of SEQ ID NO:22, the incorporation of C reflects the removal of the 3' terminal A and A residues, and the incorporation of a C (as the nucleotide complementary to the G at position 28 in the target).

Such sequence assignments flow from the known rules of base pairing. In the above-example, the incorporation of G, G, C and C could not mean that positions 26–29 of the target were CCGG, because such a nucleotide sequence is incompatible with the (known) sequence of the 3' terminus of SEQ ID NO:22. In a similar manner, consideration of the known sequences of the oligonucleotides reveals the nucleotide position being reported by a particular nucleotide of the array. In a preferred embodiment, such consideration is facilitated by performing separate sequence determinations with both a nucleotide array and its complement (such that the sequences both strands of a target molecule are obtained).

Table 4 illustrates typical oligonucleotide arrays by displaying sets of oligonucleotides sufficient to permit sequence analysis of exon 23 of the human BRCA1 gene (E23) and cystic fibrosis (CF) (at the locus of nucleotide 549) genes with a Klenow class polymerase. In the Table, the sign (+/−) indicates the strand of the target being sequenced; the number (1–6) indicates the position of the target being interrogated.

TABLE 4

| SEQ ID NO | Oligo | Nucleotide Sequence |
|---|---|---|
| 24 | E23 + 1 | CTTGTGCTGACTTACCAGATGGGAC |
| 25 | E23 + 2 | TTGTGCTGACTTACCAGATGGGACA |
| 26 | E23 + 3 | TGTGCTGACTTACCAGATGGGACAC |
| 27 | E23 + 4 | GTGCTGACTTACCAGATGGGACACT |
| 28 | E23 + 5 | TGCTGACTTACCAGATGGGACACTC |
| 29 | E23 + 6 | GCTGACTTACCAGATGGGACACTCT |
| 30 | E23 − 1 | GTCATTAATGCTATGCAGAAAATCT |
| 31 | E23 − 2 | TCATTAATGCTATGCAGAAAATCTT |
| 32 | E23 − 3 | CATTAATGCTATGCAGAAAATCTTA |
| 33 | E23 − 4 | ATTAATGCTATGCAGAAAATCTTAG |
| 34 | E23 − 5 | TTAATGCTATGCAGAAAATCTTAGA |
| 35 | E23 − 6 | TAATGCTATGCAGAAAATCTTAGAG |
| 36 | CF549 + 1 | AAAGAAATTCTTGCTCGTTGACCTC |
| 37 | CF549 + 2 | AAGAAATTCTTG-CTCGTTGACCTCC |
| 38 | CF549 + 3 | AGAAATTCTTGCTCGTTGACCTCCA |
| 39 | CF549 + 4 | GAAATTCTTGCTCGTTGACCTCCAC |
| 40 | CF549 + 5 | AAATTCTTGCTCGTTGACCTCCACT |
| 41 | CF549 − 1 | TTCTTGGAGAAGGTGGAATCACACT |
| 42 | CF549 − 2 | TCTTGGAGAAGGTGGAATCACACTG |
| 43 | CF549 − 3 | CTTGGAGAAGGTGGAATCACACTGA |
| 44 | CF549 − 4 | TTGGAGAAGGTGGAATCACACTGAG |
| 45 | CF549 − 5 | TGGAGAAGGTGGAATCACACTGAGT |

As will be recognized, the use of a Klenow class polymerase permits sequence determinations using far fewer than the maximum number of oligonucleotides that would otherwise be required. Nevertheless, because repair of mismatches may complicate analysis, Thermosequenase class polymerases are the preferred polymerases of the present invention. Since such polymerases do not repair mismatches, they are preferably used in embodiments in which oligonucleotides having all possible permutations of 3' sequence are provided, or more preferably, in embodiments in which two oligonucleotide arrays are employed (one complementary to one strand, and the other complementary to the second strand).

B. Random Nested Arrays

Whereas the non-random nested array method described above is predicated on providing the target molecule with hybridization oligonucleotides that possess the exact-sequence of the target, the random nested array method is predicated on deriving sequence information from the pattern of oligonucleotides of the array that are extended in the GBA™ reaction as well as from the identity of the nucleotide added to each extended oligonucleotide.

In the method, an array of oligonucleotide primers is employed. The lengths of the primers are most preferably uniform, and can vary from 6–20 nucleotides in length. For an array of N nucleotides, there are $4^N$ possible sequence permutations. However, because each oligonucleotide can (if hybridized to target in a GBA™ reaction) be extended by one nucleotide, the use of an array of random primers of N nucleotides in length can generate sequence information for $4^{N+1}$ nucleotides. Hence, an array of 4,096 oligonucleotides (comprising a random permutation of all possible 6-mers) could simultaneously sequence 16,384 bases of a target molecule.

The random array method may be illustrated as follows. An array of all possible 6-mers is prepared such that the x,y array location and sequence of each oligonucleotide of the array is known. Each array position is incubated with the same target polynucleotide, and a GBA™ reaction is conducted for each array position. These parallel (or sequential) reactions lead to the formation of a sequence signature consisting of array positions whose oligonucleotides have not been extended, and those whose oligonucleotides have been extended by addition of A, T, C or G.

One array position for an extended oligonucleotide is selected at random (although, in a preferred automated mode, multiple positions may be processed in parallel). The sequence of the extended oligonucleotide at the selected array position is determined using the oligonucleotide's initial (predefined 6-mer sequence) and the identity of the labeled nucleotide added to the oligonucleotide's 3' terminus in the GBA™ reaction. This determination defines a second 6-mer oligonucleotide (consisting of nucleotides 2–7 of the selected oligonucleotide). The array location of this second 6-mer position is identified, and the extension product formed by the oligonucleotide at that array position is determined. Such sequence information defines a third 6-mer oligonucleotide (consisting of nucleotides 2–7 of the second selected oligonucleotide). In like manner, the entire sequence stored in the array can be deduced.

A salient feature of the use of the GBA™ reaction in accordance with the methods of the present invention is the capacity to miniaturize such methods, resulting in a savings of space, reagents, and time, and providing increased throughput and reliability.

III. Microminiaturized Analysis Method

In one embodiment, a microminiaturized analysis format is employed. As used herein, a microminiaturized reaction is one conducted in a reaction volume of greater than 50 µl, but less than 200 µl, and most preferably less than 100 µl. Such analysis is most preferably conducted in 96 well microtiter well plates, using the indirect fluorescent colorimetry method of Huang, Z. et al. (*Anal Biochem* 207:32–39 (1992)), and the use of liquid handling robots to deliver reagents.

A preferred format involves designing the GBA™ primers so that they are associated with biotinylated spacer arms sufficient to permit them to become bound to a glass or plastic support (such as a glass slide, etc.). This attachment approach has the advantage of high specificity and results in minimal nonspecific backgrounds during attachment and hybridization. A preferred glass slide support for oligonucleotide immobilization has wells of exposed glass surrounded by a hydrophobic Teflon coating (Cel-line Associates, Inc.). The plates have 12 wells (7 mm in diameter), and are designed such that solutions can be dispensed with standard, multichannel pipetting instruments, and signals can be read on existing plate readers. Avidin will be covalently attached onto a glass-slide using our proprietary attachment chemistry. A 50 µl solution of 0.4 µm biotinylated oligonucleotide will then be added to each well, and incubated for 2 hrs, then rinsed with TNTw (10 mM Tris-HCl, pH7.5, 150 mM NaCl, 0.05% Tween-20).

IV. Nanominiaturized Analysis Method

In an alternate embodiment, a nanominiaturized analysis format is employed. As used herein, a microminiaturized reaction is one conducted in a reaction volume of less than 50 µl, and most preferably less than 10 µl.

In a preferred nanominiaturized embodiment, the support will be an etched glass plates that will hold several hundred to several thousand nanowells (0.1–5 µl volume per well), such that entire arrays can be evaluated simultaneously. The determination of the result of the GBA™ reaction will most preferably be performed via a automated processing using, for example a pixel by pixel CCD camera equipped to distinguish the labels of the nucleotides being employed. Detection of the extension may be accomplished using a variety of labels, however, two detection schemes are preferred i) direct fluorescence detection on glass, and ii) enzyme-mediated fluorescence detection.

Having now generally described the invention, the same will be more readily understood through reference to the following examples which are provided by way of illustration, and are not intended to be limiting of the present invention, unless specified.

EXAMPLES

Example 1

Nested GBA™ Analysis

In order to demonstrate the biochemical feasibility of adapting GBA™ technology to determine all 4 bases at each nucleotide position within a string of sequence, the following N-GBA™ experiment was conducted. A target polynucleotide having the sequence:

(Wild-type) 5' CCAGAAGAAA GGGCCTTCAC AGTGTCCTTT

ATGTAAGAAT GATATAACC-3'   SEQ ID NO:46 or (Mutant) 5' CCAGAAGAAA GGGCCTTCAC AGGGTCCTTT

ATGTAAGAAT GATATAACC-3'   SEQ ID NO:47 was interrogated with a set of primers that had been immobilized on to the surface of a 96 well microtiter plate in order to type the central five bases (shown in boldface) of the "wild-type" sequence (AGTGT) and of a single-base "mutant"sequence (AGGGT). The primers used had the following sequence:

(Primer 1) 5' GGTTATATCATTCTTACATAAAGG 3'
   SEQ ID NO:48

(Primer 2) 5' GTTATATCATTCTTACATAAAGGA 3'
   SEQ ID NO:49

(Primer 3) 5' TTATATCATTCTTACATAAAGGAC 3'
   SEQ ID NO:50

(Primer 4) 5' TATATCATTCTTACATAAAGGACA 3'
   SEQ ID NO:51

(Primer 5) 5' ATATCATTCTTACATAAAGGACAC 3'
   SEQ ID NO:52

Two commercially available DNA polymerases, the Klenow fragment of *E. coli* DNA polymerase I and the thermostable Thermosequenase (USB), were used for the single-base extension reaction. Primers were immobilized onto polystyrene plate via cationic detergent (Octyldimethylamine) promoted passive adsorption (Nikiforov, T. T. et al., *Anal Biochem* 227:201–209 (1995)) at defined locations. The wild-type and mutant templates were hybridized to the immobilized GBA™ primers, and the 3' end of the GBA™ primers were extended by a single fluorescent labeled chain terminator ddNTP by either Klenow or Thermosequenase. Enzyme-mediated fluorescence signal were obtained using the Cytofluor II fluorescent plate reader. The results of the experiment are shown in Table 5.

As shown in Table 5, the final calorimetric readouts from the extensions of Klenow fragment and Thermosequenase with the matching primer set and wild-type template were consistent with the true base sequence. When the mutant template was present, however, the two DNA polymerases gave quite different readout patterns. Klenow, known for its 3' to 5' exonuclease activity, was able to correct the 3' base mismatches of Primers 4 and 5 with the mutant template and extend only the C base from these primers. On the other hand, Thermosequenase could not repair and extend at any of these mismatches, resulting a lack of signal for both Primers 4 and 5. Either enzyme could produce very distinct and differential patterns of colorimetric readout for the wild-type and mutant templates, demonstrating the use of this N-GBA™ approach to screen for mutations.

TABLE 5

| Template | Primer Used | Polymerase Klenow Base Extended | | | |
|---|---|---|---|---|---|
| | | A | G | T | C |
| Wild-type | Primer 1 | 2.0 | 0.43 | 0.15 | 0.24 |
| | Primer 2 | 0.94 | 0.42 | 0.16 | 2.0 |
| | Primer 3 | 2.0 | 0.30 | 0.15 | 0.79 |
| | Primer 4 | 0.50 | 0.15 | 0.19 | 1.9 |
| | Primer 5 | 0.28 | 0.14 | 1.7 | 0.55 |
| Mutant | Primer 1 | 0.96 | 0.45 | 0.15 | 0.16 |
| | Primer 2 | 0.88 | 0.43 | 0.17 | 1.1 |
| | Primer 3 | 0.55 | 0.33 | 0.23 | 1.8 |
| | Primer 4 | 0.26 | 0.16 | 0.10 | 1.3 |
| | Primer 5 | 0.25 | 0.15 | 0.11 | 1.3 |

| | | Thermosequenase Base Extended | | | |
|---|---|---|---|---|---|
| | | A | G | T | C |
| Wild-type | Primer 1 | 2.2 | 0.28 | 0.11 | 0.14 |
| | Primer 2 | 0.33 | 0.18 | 0.15 | 2.1 |
| | Primer 3 | 2.1 | 0.16 | 0.12 | 0.22 |
| | Primer 4 | 0.20 | 0.11 | 0.15 | 2.1 |
| | Primer 5 | 0.15 | 0.12 | 2.2 | 0.16 |
| Mutant | Primer 1 | 1.2 | 0.19 | 0.11 | 0.12 |
| | Primer 2 | 0.23 | 0.19 | 0.18 | 1.3 |
| | Primer 3 | 0.22 | 0.14 | 0.13 | 1.5 |
| | Primer 4 | 0.10 | 0.10 | 0.10 | 0.16 |
| | Primer 5 | 0.10 | 0.10 | 0.15 | 0.14 |

Overall, this data reveals two important points: 1) Thermosequenase reduced template dependent noise due to its better S:N ratios when compared to Klenow, and 2) Thermosequenase did not extend at a non-specific base (i.e., it stopped when the primer overlapped the non-specific base), thus clearly indicating a mismatch which can be used to locate the position of the mutation. These advantages suggest that the exonuclease-free Thermosequenase enzyme is better suited to the N-GBA™ technology, however, since Thermosequenase does not give false data at a mismatch, SCAN™ must also be performed from the other strand to determine the sequence that follows the mutation.

Example 2

Nested GBA™ Analysis On Glass Slides

The feasibility of conducting nested GBA™ (N-GBA™) reactions on glass slides was evaluated. For this purpose, 25-mer GBA™ primers were 5' specifically attached onto the surface of a glass slide via avidin-biotin affinity interactions. The glass slides had wells of exposed glass surrounded by hydrophobic Teflon coating (Cel-line Associates, Inc.). The 12 wells were 7 mm in diameter, and were designed such that solutions could be dispensed with standard, multichannel pipetting instruments, and signals could be read on existing plate readers. A 50 μl solution of 0.4 m biotinylated oligonucleotide was added to each well, incubated for 2 hrs (1.5 mM NaCl, 10 mM EDTA, and 0.5 μM target synthetic template strands), and then rinsed with TNTw (10 mM Tris-HCl, pH7.5, 150 mM NaCl, 0.05% Tween-20).

GBA™ biochemistry (Nikiforov, T. T. et al., *Nucl Acids Res* 22:4167–4175 (1994); Nikiforov, T. T. et al., *PCR Methods and Apps* 3:285–291 (1994), both herein incorporated by reference) was used to analyze the synthetic templates; each synthetic template was split into four different wells, and each well was treated with extension mix containing all the extension reaction components, exonuclease free Klenow fragment of *E.coli* polymerase, and each of four fluorescein-labeled ddNTPs and co-ddNTPs. Enzyme-mediated fluorescence signal were obtained using the Cytofluor II fluorescent plate reader. Synthetic template 1 was designed to give a GBA™ signal in base A, and synthetic template 2 was designed to give a GBA™ signal in base G.

The GBA™ extension reactions are detected using the enzyme-mediated fluorescence precipitation method (Huang, Z. et al., *Anal Biochem* 207:32–39 (1992); Huang, Z. et al., *J Histochem Cytochem* 41:313–317 (1993)). The glass slide containing the fluorescein GBA™ signal are incubated for about 30 minutes with anti-fluorescein alkaline phosphatase solution under a blocking condition commonly used in ELISA or histochemical procedures. After washing, a droplet of an alkaline phosphatase fluorogenic precipitating substrate solution (Molecular Probes) is applied to either individual reaction wells or the entire slide. Following a 15 minute incubation and wash, the GBA™ signal can be immediately visualized under a conventional fluorescent microscope equipped with a 360 nm excitation filter and a 530 nm emission filter, or quantitated by a fluorescence microtiter plate scanner (Cytofluor II) equipped with the same filter set.

The results of this experiment are shown in FIG. 1. The results were as expected: both templates gave strong signals in correct bases with virtually no noise in other bases observed (the S:N ratio ranged from 28 to 14.2). This experiment demonstrated the feasibility of performing GBA™ biochemistry on glass, and detection of GBA™ signal using sensitive enzyme-mediated fluorescence detection using a commercially available fluorescent plate reader, the Cytofluor II. The high quality of the results strongly suggest that the proposed N-GBA™ biochemistry should perform very well on glass surface when combined with the enzyme-mediated fluorescence detection, and puts us on the path towards a low-cost miniaturizable GBA™ processing format.

Example 3

Nested GBA™ Analysis of the BRCA1 Gene

The feasibility of utilizing the nested GBA™ (N-GBA™) approach to accurately identify mutations in exon 23 of the human BRCA1 gene was evaluated. Mutations in the human BRCA1 gene have been implicated as correlated with familial breast cancer. In particular, a mutation located at position 354–359 of the normal (wild-type) sequence (TAGAGT) has been correlated with familial breast cancer. Primers having the sequences SEQ ID Nos:24–29 and 30–35 were used to sequence sample BRCA1 genes (Table 6).

TABLE 6

| SEQ ID NO 53 | Oligo | Nucleotide Sequence of E23 TCTTAGAGTGTCCCATCTGGTAAGTCAGCACAAG |
|---|---|---|
| 24 | E23 + 1 | CTTGTGCTGACTTACCAGATGGGAC |
| 25 | E23 + 2 | TTGTGCTGACTTACCAGATGGGACA |
| 26 | E23 + 3 | TGTGCTGACTTACCAGATGGGACAC |
| 27 | E23 + 4 | GTGCTGACTTACCAGATGGGACACT |
| 28 | F23 + 5 | TGCTGACTTACCAGATSGGACACTC |
| 29 | E23 + 6 | GCTGACTTACCAGATGGGACACTCT |

| SEQ ID NO 54 | Oligo | Nucleotide Sequence GACACTCTAAGATTTTCTGCATAGCATTAATGAC |
|---|---|---|
| 30 | E23 − 1 | GTCATTAATGCTATGCAGAAAATCT |
| 31 | E23 − 2 | TCATTAATGCTATGCAGAAAATCTT |
| 32 | E23 − 3 | CATTAATGCTATGCAGAAAATCTTA |
| 33 | E23 − 4 | ATTAATGCTATGCAGAAAATCTTAG |
| 34 | E23 − 5 | TTAATGCTATGCAGAAAATCTTAGA |
| 35 | E23 − 6 | TAATGCTATGCAGAAAATCTTAGAG |

Thus nestedGBA™ reactions were performed using Klenow and exo-Klenow pblymerase, and fluorocein labeled ddNTPs. The results of this experiment are shown in Table 7.

TABLE 7

Nested GBA ™ Reaction Using "+" Template Strand of E23 of BRCA1

| Primer Used | A | | C | | G | | T Signal | TIN |
|---|---|---|---|---|---|---|---|---|
| | Signal | TIN | Signal | TIN | Signal | TIN | | |
| | Nucleotide Extended Using Exo-Klenow | | | | | | | |
| E23+1 | 3.07 | 0.15 | 0.93 | 0.12 | 0.38 | 0.19 | 0.38 | 0.12 |
| E23+2 | 0.94 | 0.14 | 2.97 | 0.15 | 0.35 | 0.16 | 0.45 | 0.14 |
| E23+3 | 0.42 | 0.11 | 0.41 | 0.10 | 0.26 | 0.11 | 2.28 | 0.10 |
| E23+4 | 0.49 | 0.15 | 3.21 | 0.16 | 0.38 | 0.34 | 0.75 | 0.16 |
| E23+5 | 0.37 | 0.14 | 0.49 | 0.14 | 0.31 | 0.14 | 2.70 | 0.13 |
| E23+6 | 3.13 | 0.22 | 0.40 | 0.18 | 0.62 | 2.82 | 0.62 | 0.16 |
| | Nucleotide Extended Using Klenow | | | | | | | |
| E23+1 | 3.34 | 0.38 | 1.38 | 0.21 | 0.81 | 0.21 | 0.41 | 0.15 |
| E23+2 | 1.55 | 0.35 | 2.96 | 0.15 | 0.58 | 0.19 | 0.44 | 0.17 |
| E23+3 | 1.04 | 0.38 | 1.17 | 0.13 | 0.52 | 0.16 | 3.08 | 0.12 |
| E23+4 | 1.03 | 0.57 | 3.35 | 0.13 | 0.69 | 0.45 | 1.29 | 0.22 |
| E23+5 | 0.57 | 0.12 | 1.54 | 0.15 | 0.47 | 0.31 | 3.34 | 0.19 |
| E23+6 | 3.36 | 0.31 | 0.88 | 0.17 | 1.41 | 1.64 | 1.12 | 0.18 |

The results shown in Table 7 thus show that Klenow and Exo-Klenow gave the same sequence (ACTCTA) for the primer extension, thereby indicating that the "+" strand of the E23 locus being sequenced had the complementary sequence (5' TAGAGT 3'). To confirm this result, a nested GBA™ reaction was performed using the "−" template strand of E23 of BRCA1. The results of this experiment are shown in Table 8.

TABLE 8

Nested GBA ™ Reaction Using "−" Template Strand of E23 of BRCA1

| Primer Used | A Signal | TIN | C Signal | TIN | G Signal | TIN | T Signal | TIN |
|---|---|---|---|---|---|---|---|---|
| Nucleotide Extended Using Exo-Klenow | | | | | | | | |
| E23-1 | 0.54 | 0.08 | 0.28 | 0.11 | 0.43 | 0.22 | 2.00 | 0.12 |
| E23-2 | 2.04 | 0.09 | 0.19 | 0.08 | 0.31 | 0.08 | 0.68 | 0.08 |
| E23-3 | 0.69 | 0.11 | 0.16 | 0.10 | 3.29 | 0.09 | 0.48 | 0.08 |
| E23-4 | 3.15 | 0.36 | 0.18 | 0.14 | 0.44 | 0.10 | 0.69 | 0.09 |
| E23-5 | 0.26 | 0.14 | 0.17 | 0.09 | 2.34 | 0.10 | 1.00 | 1.37 |
| E23-6 | 0.38 | 0.10 | 0.24 | 0.09 | 0.47 | 0.09 | 2.57 | 0.24 |
| Nucleotide Extended Using Klenow | | | | | | | | |
| E23-1 | 0.47 | 1.24 | 0.78 | 0.12 | 0.66 | 0.37 | 3.43 | 0.70 |
| E23-2 | 1.78 | 0.12 | 0.26 | 0.08 | 0.24 | 0.1 | 0.96 | 0.11 |
| E23-3 | 1.48 | 0.16 | 0.31 | 0.09 | 3.42 | 0.24 | 0.97 | 0.51 |
| E23-4 | 3.30 | 0.22 | 0.29 | 0.08 | 0.80 | 0.15 | 0.72 | 0.30 |
| E23-5 | 0.53 | 0.22 | 0.17 | 0.09 | 2.29 | 0.11 | 2.57 | 1.85 |
| E23-6 | 0.73 | 0.14 | 0.25 | 0.11 | 0.95 | 0.17 | 3.48 | 0.42 |

The results shown in Table 8 thus show that Klenow and Exo-Klenow gave the same sequence (TAGAGT) for the primer extension, thereby indicating that the "−" strand of the E23 locus being sequenced had the complementary sequence (5' ACTCTA 3').

In order to demonstrate the ability of the present invention to discern mutations in the E23 locus, two additional experiments were performed. In the first experiment, a target strand having a deletion of the AG nucleotides was analyzed. In the second, a mixture of the normal and AG deletion target template was made, and analyzed via the nested GBA™ method. The first experiment thus discerns the profile that would be presented by an individual having a homozygous mutation in the E23 locus, while the second experiment analyzes the profile that would be presented by an individual having heterogygosity in this region. The results of these experiments are shown in Tables 9 and 10.

TABLE 9

Nested GBA ™ Reaction Using "AG" Deletion in "+" Template Strand of E23 of BRCA1

| Primer | A Signal | C Signal | G Signal | T Signal |
|---|---|---|---|---|
| E23 + 1 | 2.77 | 0.13 | 0.11 | 0.1 |
| E23 + 2 | 0.22 | 2.45 | 0.11 | 0.11 |
| E23 + 3 | 0.12 | 0.13 | 0.1 | 1.51 |
| E23 + 4 | 2.53 | 0.1 | 0.1 | 0.11 |
| E23 + 5 | 1.53 | 0.1 | 0.11 | 0.12 |
| E23 + 6 | 0.24 | 0.11 | 0.61 | 0.13 |

The results shown in Table 9 define an extended sequence for this sample of ACTAA, thereby indicating that the "+" strand of the E23 locus being sequenced had the complementary sequence (5' TTAGT 3') (see SEQ ID NO:53). The observed sequence is explained as follows: Primers 1–3 sequence bases that precede the deletion, and hence report the wild-type sequence (ACT). Primer 4, which ends just before the deletion, reports the sequence of the first nucleotide of the target strand that follows deletion (i.e., A). Primer 5, when hybridized to the deletion ends with a one base mismatch, which is removed by the polymerase. The truncated hybridized primer 5 then sequences the same nucleotide as that sequenced by Primer 4. Primer 6, which has a two base mismatch is not extended in the reaction.

TABLE 10

Nested GBA ™ Reaction Using A Mixture Of Templates "AG" Deletion And Normal "+" Template Strand of E23 of BRCA1

| Primer: | A Signal | C Signal | G Signal | T Signal |
|---|---|---|---|---|
| E23 + 1 | 3.31 | 0.39 | 0.34 | 0.36 |
| E23 + 2 | 0.5 | 2.87 | 0.39 | 0.41 |
| E23 + 3 | 0.29 | 0.35 | 0.33 | 1.51 |
| E23 + 4 | 1.97 | 2.53 | 0.38 | 0.4 |
| E23 + 5 | 0.51 | 0.38 | 0.53 | 1.64 |
| E23 + 6 | 3.21 | 0.4 | 0.41 | 0.43 |

Table 10 reveals that Primers 1–3 were extended as expected to yield extension products A, C, and T, respectively for both wild-type and AG deletion target molecules. The presence of wild-type target results in the extension of Primer 4 with a C residue (consistent with the results obtained above; see Table 7). Similarly, the presence of the wild-type target causes Primers 5 and 6 to be extended by T and A, respectively (see Table 7). The presence of the AG deletion target causes Primer 4 to be extended by an A (consistent with the result shown in Table 9). Consistent with the fact that the target mixture is 1:1 wild-type:mutant, the signals of A and C addition for Primer 4 are approximately equal. Neither Primer 5 nor Primer 6 are extended when hybridized to the AG deletion target because their 3' terminal nucleotides would not be base-paired with the AG deletion target mutant. The failure of Primer 5 to be extended when hybridized to the AG mutant reflects the relatively lower binding avidity of the polymerase for Primer 5:mutant duplexes as compared to Primer 5:wild-type duplexes (in which there would be no mismatch).

Example 4

Nested GBA™ Analysis of the CF Gene

The feasibility of utilizing the nested GBA™ (N-GBA™) approach to accurately identify mutations in the nucleotide 549 locus of the human CF gene was also evaluated.

Thus, a set of primers (shown in Table 11) was prepared, and used in a nested GBA ™ reaction to sequence a locus of the cystic fibrosis gene (CF) around nucleotide 549.

TABLE 11

| SEQ ID NO | Oligo | Nucleotide Sequence |
|---|---|---|
| 55 | Oligo | CTGAGTGGAGGTCAACGAGCAAGAATTTCTTT |
| 36 | CF549 + 1 | AAAGAAATTCTTGCTCGTTGACCTC |
| 37 | CF549 + 2 | AAGAAATTCTTGCTCGTTGACCTCC |
| 38 | CF549 + 3 | AGAAATTCTTGCTCGTTGACCTCCA |
| 39 | CF549 + 4 | GAAATTCTTGCTCGTTGACCTCCAC |
| 40 | CF549 + 5 | AAATTCTTGCTCGTTGACCTCCACT |
| SEQ ID NO | Oligo | Nucleotide Sequence |
| 56 | Oligo | TCCACTCAGTGTGATTCCACCTTCTCCAAGAA |
| 41 | CF549 − 1 | TTCTTGGAGAAGGTGGAATCACACTG |
| 42 | CF549 − 2 | TCTTGGAGAAGGTGGAATCACACTG |
| 43 | CF549 − 3 | CTTGGAGAAGGTGGAATCACACTGA |
| 44 | CF549 − 4 | TTGGAGAAGGTGGAATCACACTGAG |

TABLE 11-continued

| 45 | CF549 – 5 | TGGAGAAGGTGGAATCACACTGAGT |
|----|-----------|---------------------------|

Table 12 shows the result of this experiment with respect to the "+" strand of this target molecule.

TABLE 12

Nested GBA ™ Reaction Using "+" Template Strand of CF Gene At Locus 549

| Primer Used | A | | C | | G Signal | TIN | T Signal | TIN |
|---|---|---|---|---|---|---|---|---|
| | Signal | TIN | Signal | TIN | | | | |
| Nucleotide Extended Using Exo-Klenow | | | | | | | | |
| CF549+1 | 0.25 | 0.09 | 2.99 | 0.Q9 | 0.20 | 0.09 | 0.29 | 0.09 |
| CF549+2 | 3.49 | 0.10 | 0.74 | 0.10 | 0.19 | 0.10 | 0.25 | 0.10 |
| CF549+3 | 1.01 | 0.31 | 3.23 | 0.12 | 0.26 | 0.13 | 0.38 | 0.12 |
| CF549+4 | 0.47 | 0.19 | 0.89 | 0.16 | 0.56 | 0.25 | 2.76 | 0.14 |
| CF549+5 | 0.30 | 0.11 | 2.97 | 0.12 | 0.21 | 0.13 | 0.39 | 0.12 |
| Nucleotide Extended Using Klenow | | | | | | | | |
| CF549+1 | 0.43 | 0.15 | 3.37 | 0.10 | 0.29 | 0.15 | 0.82 | 0.64 |
| CF549+2 | 3.45 | 0.36 | 1.38 | 0.10 | 0.33 | 0.22 | 0.48 | 0.14 |
| CF549+3 | 1.52 | 0.13 | 3.60 | 0.11 | 0.36 | 0.18 | 0.51 | 0.11 |
| CF549+4 | 1.41 | 0.17 | 1.87 | 0.13 | 0.92 | 0.26 | 3.48 | 0.15 |
| CF549+5 | 0.60 | 0.11 | 3.22 | 0.12 | 0.28 | 0.15 | 0.59 | 0.11 |

As indicated in Table 12, both Klenow and Exo-Klenow gave nested GBA™ extension products of C, A, C, T and C, respectively for primers CF549+through CF549+5. The deduced sequence for the 549 locus of the target is therefore GAGTG, as expected. The results obtained above were confirmed by performing a nested GBA™ reaction using the "–" CF strand. The results of his experiment are presented in Table 13.

TABLE 13

Nested GBA ™ Reaction Using "–" Template Strand of CF Gene At Locus 549

| Primer Used | A | | C | | G Signal | TIN | T Signal | TIN |
|---|---|---|---|---|---|---|---|---|
| | Signal | TIN | Signal | TIN | | | | |
| Nucleotide Extended Using Exo-Klenow | | | | | | | | |
| CF549-1 | 0.37 | 0.11 | 0.28 | 0.15 | 3.09 | 0.10 | 0.45 | 0.13 |
| CF549-2 | 3.32 | 0.11 | 0.25 | 0.13 | 0.52 | 0.13 | 0.27 | 0.12 |
| CF549-3 | 1.65 | 0.12 | 0.19 | 0.19 | 3.88 | 0.13 | 1.34 | 0.19 |
| CF549-4 | 0.69 | 0.09 | 0.11 | 0.12 | 1.16 | 0.10 | 2.97 | 0.09 |
| CF549-5 | 1.10 | 0.12 | 0.56 | 0.31 | 3.45 | 0.54 | 1.45 | 0.15 |
| Nucleotide Extended Using Klenow | | | | | | | | |
| CF549-1 | 1.31 | 0.13 | 0.77 | 0.53 | 3.37 | 0.17 | 1.21 | 0.21 |
| CF549-2 | 3.52 | 0.13 | 0.74 | 0.63 | 1.36 | 0.15 | 0.89 | 0.21 |
| CF549-3 | 1.65 | 0.12 | 0.19 | 0.19 | 3.88 | 0.13 | 1.34 | 0.19 |
| CF549-4 | 0.69 | 0.09 | 0.11 | 0.12 | 1.16 | 0.10 | 2.97 | 0.09 |
| CF549-5 | 1.10 | 0.12 | 0.56 | 0.31 | 3.45 | 0.54 | 1.45 | 0.15 |

As indicated in Table 13, both Klenow and Exo-Klenow gave nested GBA™ extension products of G, A, G, T and G, respectively for primers CF549-1 through CF549-5. The deduced sequence for the 549 locus of the target is therefore CACTC, as expected. The results obtained above were confirmed by performing a nested GBA™ reaction using the "–" CF strand. The results of this experiment are presented in Table 13. Klenow, Exo-Klenow and Sequenase were compared for their ability to serve as the polymerase in the nested GBA™ reaction shown in Example 13. The enzymes gave equivalent N-GBA™ results.

Example 5

Nested GBA™ Analysis of Hot Spots in the p53 Gene

The feasibility of utilizing the nested GBA™ (N-GBA™) approach to accurately detect p53 mutations was evaluated.

The p53 gene encompasses an approximately 19 kilobase stretch, comprising 11 exons (393 codons), of chromosome region 17p13.105–p12. Characterized as a tumor antigen in 1979, then as an oncogene, and finally as a tumor suppressor gene, p53 has received increasing study in cancer research. Mutations in the p53 gene are the single most common genetic alteration in human cancers and generally result in loss of function of the protein. The p53 protein's apparent role in regulating cell growth and apoptosis suggests it is a core protein in determination of tumorigenesis, with mutations in p53 being part of the cascade necessary for the development of many tumors. Three quarters of colon cancers and half of lung and breast cancers have been reported to contain p53 mutations (Levine, A. J., Canc. Surveys 12:59–79 (1992); herein incorporated by reference). Since more than 100,000 additional cases of each of these cancers is diagnosed each year, the potential application of p53 analysis is significant both clinically and commercially. The majority of p53 mutations are missense (ranging from 75% to more than 90%), tightly clustered between codons 118 and 309, the DNA binding region of the protein. Amino acids 175, 248, 249, 273, and 282 account for 40% of the total reported missense mutations, and the predominance of these so-called "hot-spots" vary depending on the tissue of origin of the cancer. The diversity and dispersion of clinically relevant mutations poses a significant challenge to the development of routine detection strategies. Because of the high prevalence of p53 mutations in a wide variety of common cancers and the large number of potential mutations in a defined gene region, p53 is an excellent target for development of a sequence composition/confirmation analysis tool such as SCAN™.

Figure 2:
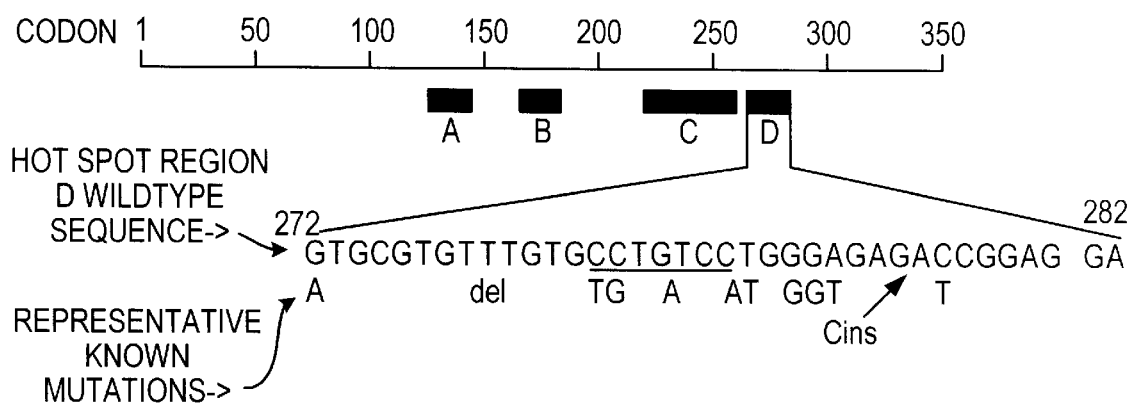
FIG. 2 shows the four major p53 mutational hot-spot regions containing most cited p53 mutations are indicated by the black bars marked A–D: A=codons 132–143, B=codons 174–179, C=codons 236–258 and D=codons 272–282 (del= deletion; ins=insertion).

Nested GBA™ primers were designed for all DNA bases in a hot-spot (codons 272–282) of the target p53 gene. FIG. 2 displays the four mutational hot-spot regions of p53 gene with the wild-type and known representative mutant sequences of codons 272 to 282 (region D) highlighted. Specifically, three synthetic templates are designed to match three DNA samples, each containing a mutation in either codon 273, 275, or 281. Two additional synthetic templates are designed to be representative of a deletion mutation (codons 266 and 267 deleted) and an insertion mutation (C insertion at codon 280).

One PCR primer for the each primer set will have four phosphorothioate linkages at its 5' end in preparation for TargEx™ treatment. TargEx™ is a method developed to quantitatively convert double-stranded PCR product into single-stranded DNA by selectively degrading one of the strands with bacteriophage T7 gene 6 exonuclease (Nikiforov, T. T. et al., Nucl Acids Res 22:4167–4175 (1994); Nikiforov, T. T. et al., PCR Methods and Apps 3:285–291 (1994)). Specifically, PCR product amplified from human genomic DNA using one fluorescein-labeled, phosphorothioated PCR primer and one unmodified primer are treated with T7 gene 6 exonuclease (U.S. Biochemical) at a final concentration of 2U/μl PCR (diluted in buffer supplied by manufacturer). After 1 hr of incubation at room temperature, NaCl and EDTA are added to a concentration of 1.5M and 10 mM, respectively, to stop the exonuclease digestion. The mixture is then applied to the immobilized GBA™ primer for subsequent hybridization and extension. After extension, the standard ABI fluorescent cycle sequencing system is used to analyze the reaction.

The 5' end of the primers are specifically attached to glass slides to form a SCAN™ array. Synthetic oligonucleotide templates corresponding to portions of the target hot-spot and containing various known mutations are used to test the array and the GBA™ biochemistry to demonstrate that robust, unambiguous (low noise and background) data can be obtained from such an analysis. Permutations of the standard GBA™ biochemistry, in particular the use of different DNA polymerases, are evaluated to ensure optimal signal:noise (S:N) characteristics for all 4 nucleotides in the feasibility test system.

Primer pairs will be qualified by amplification of human genomic DNA at a concentration of 12.5 μg/ml in 30 μl reactions in 96 well V-bottom polycarbonate plates (Costar). The final concentration of the reaction mixture will be 400 μM each dNTP, 50 mM KCl, 10 mM Tris HCl (pH 8.5), 1.5 mM MgCl$_2$, 0.5 μM each primer, 2.5 ng/μl DNA, and 0.025 U/μl Taq DNA polymerase (Perkin-Elmer). Each reaction will be overlayed with 30 μl mineral oil and cycled in a BioIII thermocycler (Sun BioScience Inc., Branford Conn.). Following an initial two minute denaturation step at 94° C., 35 cycles will be carried out, each consisting of denaturation (1 min at 94° C.), annealing (2 min at 55° C.), and extension (3 min at 72° C.). Ten μl of PCR product will be run on 15% non-denaturing polyacrylamide gels at 40W for 40 min to analyze yield. The amplification products will be quantified by comparison with multiple dilutions of a Mass Marker (BRL).

Example 6

Use of Nested GBA™ Primers on PCR-Generated Templates

The performance of the Nested GBA™ method is assessed using PCR-amplified genomic DNA as the target for analysis. At least two overlapping PCR primer pairs are designed and tested on wild-type and mutant-containing genomic DNAs (five total), and the resultant PCR products tested by N-GBA™ on the SCANTS arrays produced in Example 5. The PCR products will be evaluated for hybridization and extension efficiencies relative to the synthetic templates of Example 5 to ensure that analysis of PCR products is equally robust.

Example 7

Analysis of Primer Extension at Position of 3' Terminal Nucleotide Mismatch An experiment was performed in order to determine the capacity of varios polymerases to extend a primer having a mismatch at its 3' terminus. Two 6-mer primers were prepared and were separately hybridized to each member of a set of four template molecules whose sequences differed only in the idenity of the 6th nucleotide, as shown in Table 14. In Table 14, "X" denotes the 3' terminal nucleotide of the primer; "Y" denotes the nucleotide of the template that is opposite to "X" when the primer and template are hybridize to one another.

TABLE 14

| SEQ ID NO. | Molecule | Nucleotide Sequence | Nucleotide X | Nucleotide Y |
|---|---|---|---|---|
|  | Primer 4248 | TATGGC | C |  |
| 57 | Template T1 | CGGTTACCATA |  | A |
| 58 | Template T2 | CGGTTCCCATA |  | C |
| 58 | Template T3 | CGGTTGCCATA |  | G |
| 60 | Template T4 | CGGTTTCCATA |  | T |
|  | Primer 4248 | TATGGA | C |  |
| 57 | Template T1 | CGGTTACCATA |  | A |
| 58 | Template T2 | CGGTTCCCATA |  | C |
| 59 | Template T3 | CGGTTGCCATA |  | G |
| 60 | Template T4 | CGGTTTCCATA |  | T |

Thus for each primer, the efficiency and capacity of extension was determine using four parallel reactions, in which three comprise efforts to extend a mismatched 3' terminus, and one comprised a control in which the 3' terminal nucleotide of the primer was correctly base paired. Extension was determined by GBA™ reaction.

The results of this experiment are shown in Table 15, with respect to four polymerases: "K" (Klenow), "exo-K" (exo-Klenow), "Bst" (Bst polymerase) and "Therm" (Thermosequenase). The data are expressed in optical density units.

Table 15 shows that Thermosequenase did not extend primers whose 3' terminal nucleotides were not based paired to the template. In contrast, Klenow and Exo-Klenow were both able to incorporate label onto the 3' terminus of 3' terminally mismatched primers, consistent with the data presented above.

TABLE 15

| Primer/ Template | X:Y | Labeled Nucleotide Present | DNA Polymerase Employed | | | |
|---|---|---|---|---|---|---|
|  |  |  | K | exo-K | Therm | Bst |
| 4748/T1 | C:A | A | 0.70 | 1.80 | 0.40 | 0.55 |
|  |  | C | 0.30 | 0.60 | 0.27 | 0.25 |
|  |  | G | 0.80 | 0.30 | 0.32 | 0.32 |
|  |  | T | 2.20 | 0.60 | 0.45 | 0.25 |
| 4748/T2 | C:C | A | 0.70 | 0.60 | 0.40 | 0.28 |
|  |  | C | 0.30 | 0.65 | 0.25 | 0.21 |
|  |  | G | 1.60 | 0.30 | 0.47 | 0.37 |
|  |  | T | 0.50 | 0.30 | 0.25 | 0.20 |
| 4748/T3 | C:G | A | 2.70 | 2,80 | 2.10 | 2.80 |
|  |  | C | 1.00 | 0.60 | 0.40 | 0.25 |
|  |  | G | 0.90 | 0.20 | 0.30 | 0.20 |
|  |  | T | 0.50 | 0.30 | 0.22 | 0.18 |
| 4748/T4 | C:T | A | 2.50 | 2.10 | 0.75 | 1.10 |
|  |  | C | 0.30 | 0.70 | 0.25 | 0.21 |
|  |  | G | 1.30 | 0.40 | 0.35 | 0.30 |
|  |  | T | 0.50 | 0.30 | 0.15 | 0.20 |
| 4749/T1 | A:A | A | 0.80 | 0.50 | 0.40 | 0.30 |
|  |  | C | 0.30 | 0.50 | 0.30 | 0.30 |
|  |  | G | 1.30 | 0.50 | 0.30 | 0.30 |
|  |  | T | 2.10 | 0.70 | 0.50 | 0.30 |
| 4749/T2 | A:C | A | 1.00 | 1.10 | 0.30 | 0.40 |
|  |  | C | 0.30 | 0.40 | 0.30 | 0.30 |
|  |  | G | 2.30 | 0.70 | 0.50 | 0.50 |
|  |  | T | 0.60 | 0.40 | 0.75 | 0.20 |
| 4749/T3 | A:G | A | 0.90 | 0.50 | 0.50 | 0.40 |
|  |  | C | 3.00 | 0.90 | 0.70 | 0.30 |
|  |  | G | 1.40 | 0.60 | 0.40 | 0.40 |
|  |  | T | 0.70 | 0.40 | 0.30 | 0.20 |
| 4749/T4 | A:T | A | 3.00 | 3.00 | 2.00 | 2.40 |
|  |  | C | 0.30 | 0.30 | 0.30 | 0.20 |
|  |  | G | 1.20 | 0.50 | 0.30 | 0.30 |
|  |  | T | 0.60 | 0.30 | 0.30 | 0.20 |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method for determining the nucleotide sequence of a nucleic acid molecule which comprises the steps of:
   (A) arraying a set of nested primer oligonucleotides onto a solid support, each array position containing a different array member having a predetermined sequence;
   (B) incubating oligonucleotides of said array in the presence of a preparation of said nucleic acid molecules, a polymerase and at least one chain terminator nucleotide; wherein said incubation is under conditions sufficient to permit DNA hybridization to occur between the oligonucleotides of said incubation and said nucleic acid molecules;
   (C)
      (1) in the case wherein the 3' terminal nucleotide of an oligonucleotide is hybridized to said nucleic acid molecule, permitting oligonucleotides hybridized to nucleic acid molecules to be extended by polymerase-mediated incorporation of a single chain terminator nucleotide residue onto the 3' terminus of said hybridized oligonucleotide, wherein for each hybridized oligonucleotide being so extended, said incorporated nucleotide residue is complementary to the nucleotide residue immediately 5' to the nucleotide residue of the nucleic acid molecule that is hybridized with that oligonucleotide's 3' terminal nucleotide residue; then performing step (D);
      (2) in the case wherein the 3' terminal nucleotide of an oligonucleotide is not hybridized to said nucleic acid molecule, either:
         (a) not permitting oligonucleotides hybridized to nucleic acid molecules to be extended by polymerase-mediated incorporation of a single chain terminator nucleotide residue onto the 3' terminus of said hybridized oligonucleotide, or
         (b) permitting the removal of any non-hybridized nucleotide residues from the 3' terminus of said hybridized oligonucleotides, so as to form a truncated primer oligonucleotide whose 3' terminus is hybridized to said nucleic acid molecule, and then permitting polymerase-mediated incorporation of a single chain terminator nucleotide residue onto the 3' terminus of said hybridized truncated oligonucleotide, wherein for each hybridized truncated oligonucleotide being so extended, said incorporated nucleotide residue is complementary to the nucleotide residue immediately 5' to the nucleotide residue of the nucleic acid molecule that is hybridized with that truncated oligonucleotide's 3' terminal nucleotide residue; then performing step (D);
   (D) determining, at each array position at which an oligonucleotide has incorporated a single chain terminator nucleotide residue, the identity of the incorporated chain terminator nucleotide residue; and
   (E) determining the nucleotide sequence of said nucleic acid molecule from the determined identity of the incorporated nucleotide of primer oligonucleotides of said array, and known sequence of the oligonucleotide at each array position.

2. The method of claim 1, wherein each array position contains a primer oligonucleotide that is capable of hybridizing to a region of said nucleic acid molecule.

3. The method of claim 1, wherein said polymerase is a Thermosequenase class polymerase.

4. The method of claim 1, wherein said polymerase is a Klenow class polymerase.

5. The method of claim 1, wherein said array is a random oligonucleotide array.

6. The method of claim 1, wherein said set of nested primer oligonucleotides comprises oligonucleotide members having all possible permutations of nucleotides over a region of from 1 to 20 bases.

7. The method of claim 1, wherein said method is conducted in the presence of at least four chain terminator nucleotide species, at least one of which is labeled.

8. The method of claim 7, wherein all of said chain terminator nucleotide species are labeled, and wherein the label of any such species can be distinguished from the label of any other species present.

9. The method of claim 1, wherein said nucleic acid molecule is a DNA molecule.

10. The method of claim 1, wherein said nucleic acid molecule is RNA.

11. The method of claim 1, wherein said method is performed both on said nucleic acid molecule, and on a complement of said nucleic acid molecule.

12. The method of claim 9, wherein said DNA is genomic DNA of a human or non-human mammal.

13. The method of claim 9, wherein said DNA is human genomic DNA.

14. The method of claim 13, wherein said DNA is suspected to contain a genetic variation associated with a disease, and said method is employed to determine whether said DNA contains said variation.

15. The method of claim 14, wherein said disease is cancer or cystic fibrosis.

16. The method of claim 1, wherein said oligonucleotides are immobilized onto said solid support.

17. The method of claim 16, wherein said support is plastic or glass.

18. The method of claim 1, wherein said set of nested primer oligonucleotides is a non-random oligonucleotide array.

19. The method of claim 1, wherein the incubation is conducted in the absence of any non-chain terminator nucleotides.

20. A kit for determining the sequence of a nucleic acid molecule which comprises a solid support containing an array of spaced apart receptacles for oligonucleotides, each receptacle containing a different primer oligonucleotide, a polymerase capable of removal of any non-hybridized nucleotide residues from the 3' terminus of a primer oligonucleotide, and at least one chain terminator nucleotide.

21. The kit of claim 20, further comprising a polymerase not having exonuclease activity.

22. The kit of claim 20, wherein each array receptacle additionally contains at least four chain terminator nucleotide species, at least on of which is labeled.

23. The kit of claim 20, wherein all of said chain terminator nucleotide species are labeled, and wherein the label of any such species can be distinguished from the label of any other species present.

24. A method for determining the nucleotide sequence of a nucleic acid molecule which comprises the steps of:
(A) providing an array of nested primer oligonucleotides on a solid support, each array position containing a different array member having a predetermined sequence;
(B) incubating the oligonucleotides of said array in the presence of a preparation of said nucleic acid molecules a polymerase and at least one chain terminator nucleotide; wherein said incubation is under conditions sufficient to permit DNA hybridization to occur between the oligonucleotides of said incubation and said nucleic acid molecule;
(C)
(1) in the case wherein the 3' terminal nucleotide of an oligonucleotide is hybridized to said nucleic acid molecule, permitting the oligonucleotide hybridized to nucleic acid molecules to be extended by polymerase-mediated incorporation of a single chain terminator nucleotide residue onto the 3' terminus of said hybridized oligonucleotide, wherein for each hybridized oligonucleotide being so extended, said incorporated nucleotide residue is complementary to the nucleotide residue immediately 5' to the nucleotide residue of the nucleic acid molecule that is hybridized with that oligonucleotide's 3' terminal nucleotide residue; then performing step (D);
(2) in the case wherein the 3' terminal nucleotide of an oligonucleotide is not hybridized to said nucleic acid molecule, either:
(a) not permitting oligonucleotides hybridized to nucleic acid molecules to be extended by polymerase-mediated incorporation of a single chain terminator nucleotide residue onto the 3' terminus of said hybridized oligonucleotide, or
(b) permitting the removal of any non-hybridized nucleotide residues from the 3' terminus of said hybridized oligonucloetides, so as to form a truncated primer oligonucleotide whose 3' terminus is hybridized to said nucleic acid molecule, and then permitting polymerase-mediated incorporation of a single chain terminator nucleotide residue onto the 3' terminus of said hybridized truncated oligonucleotide, wherein for each hybridized truncated oligonucleotide being so extended, said incorporated nucleotide residue is complementary to the nucleotide residue immediately 5' to the nucleotide residue of the nucleic acid molecule that is hybridized with that truncated oligonucleotide's 3' terminal nucleotide residue; then performing step (D);
(D) determining, at each array position at which an oligonucleotide has incorporated a single chain terminator nucleotide residue, the identity of the incorporated chain terminator nucleotide residue; and
(E) determining the nucleotide sequence of said nucleic acid molecule from the determined identity of the incorporated nucleotide of primer oligonucleotides of said array, and known sequence of the oligonucleotide at each array position.

25. The method of claim 24, wherein each array position has a primer oligonucleotide that is capable of hybridizing to a region of said nucleic acid molecule.

26. The method of claim 24, wherein said polymerase is a Thermosequenase class polymerase.

27. The method of claim 24, wherein the polymerase is a Klenow class polymerase.

28. The method of claim 24, wherein the array is a random oligonucleotide array.

29. The method of claim 24, wherein the array is a non-random oligonucleotide array.

30. The method of claim 24, wherein the incubation is conducted in the absence of any non-chain terminator nucleotides.

31. The method of claim 24, wherein said nucleic acid molecule is DNA.

* * * * *

```
                              SEQUENCE LISTING (1) GENERAL INFORMATION:

(iii) NUMBER OF SEQUENCES: 60

(2) INFORMATION FOR SEQ ID NO:1:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: YES (xi) SEQUENCE DESCRIPTION: SEQ ID NO:1:

CTTGTGCTGA CTTACCAGAT GGGAC                                           25

(2) INFORMATION FOR SEQ ID NO:2:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: YES (xi) SEQUENCE DESCRIPTION: SEQ ID NO:2:

TTGTGCTGAC TTACCAGATG GGACA                                           25

(2) INFORMATION FOR SEQ ID NO:3:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: YES (xi) SEQUENCE DESCRIPTION: SEQ ID NO:3:

TTGTGCTGAC TTACCAGATG GGACC                                           25

(2) INFORMATION FOR SEQ ID NO:4:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: YES (xi) SEQUENCE DESCRIPTION: SEQ ID NO:4:
```

TTGTGCTGAC TTACCAGATG GGACT                    25

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO:5:

TTGTGCTGAC TTACCAGATG GGACG                    25

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO:6:

TGTGCTGACT TACCAGATGG GACAA                    25

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO:7:

TGTGCTGACT TACCAGATGG GACAC                    25

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO:8:

TGTGCTGACT TACCAGATGG GACAT                    25

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO:9:

TGTGCTGACT TACCAGATGG GACAG                                              25

(2) INFORMATION FOR SEQ ID NO:10:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (xi) SEQUENCE DESCRIPTION: SEQ ID NO:10:

TGTGCTGACT TACCAGATGG GACCA                                              25

(2) INFORMATION FOR SEQ ID NO:11:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (xi) SEQUENCE DESCRIPTION: SEQ ID NO:11:

TGTGCTGACT TACCAGATGG GACCC                                              25

(2) INFORMATION FOR SEQ ID NO:12:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (xi) SEQUENCE DESCRIPTION: SEQ ID NO:12:

TGTGCTGACT TACCAGATGG GACCT                                              25

(2) INFORMATION FOR SEQ ID NO:13:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (xi) SEQUENCE DESCRIPTION: SEQ ID NO:13:

TGTGCTGACT TACCAGATGG GACCG                                              25

(2) INFORMATION FOR SEQ ID NO:14:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: YES (xi) SEQUENCE DESCRIPTION: SEQ ID NO:14:

TGTGCTGACT TACCAGATGG GACTA                                             25

(2) INFORMATION FOR SEQ ID NO:15:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: YES (xi) SEQUENCE DESCRIPTION: SEQ ID NO:15:

TGTGCTGACT TACCAGATGG GACTC                                             25

(2) INFORMATION FOR SEQ ID NO:16:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: YES (xi) SEQUENCE DESCRIPTION: SEQ ID NO:16:

TGTGCTGACT TACCAGATGG GACTT                                             25

(2) INFORMATION FOR SEQ ID NO:17:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: YES (xi) SEQUENCE DESCRIPTION: SEQ ID NO:17:

TGTGCTGACT TACCAGATGG GACTG                                             25

(2) INFORMATION FOR SEQ ID NO:18:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: YES (xi) SEQUENCE DESCRIPTION: SEQ ID NO:18:

TGTGCTGACT TACCAGATGG GACGA                                              25

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO:19:

TGTGCTGACT TACCAGATGG GACGC                                              25

(2) INFORMATION FOR SEQ ID NO:20:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO:20:

TGTGCTGACT TACCAGATGG GACGT                                              25

(2) INFORMATION FOR SEQ ID NO:21:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO:21:

TGTGCTGACT TACCAGATGG GACGG                                              25

(2) INFORMATION FOR SEQ ID NO:22:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO:22:

GTGCTGACTT ACCAGATGGG ACAAA                                              25

(2) INFORMATION FOR SEQ ID NO:23:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO:23:

CCGTACTCCC ATCTGGTAAG TCAGCACAAG                                            30

(2) INFORMATION FOR SEQ ID NO:24:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (vi) ORIGINAL SOURCE:
            (A) ORGANISM: HOMO SAPIENS (vii) IMMEDIATE SOURCE:
            (B) CLONE: EXON 23 BRCA1 GENE (xi) SEQUENCE DESCRIPTION: SEQ ID NO:24:

CTTGTGCTGA CTTACCAGAT GGGAC                                                 25

(2) INFORMATION FOR SEQ ID NO:25:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (vi) ORIGINAL SOURCE:
            (A) ORGANISM: HOMO SAPIENS (vii) IMMEDIATE SOURCE:
            (B) CLONE: EXON 23 BRCA1 GENE (xi) SEQUENCE DESCRIPTION: SEQ ID NO:25:

TTGTGCTGAC TTACCAGATG GGACA                                                 25

(2) INFORMATION FOR SEQ ID NO:26:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (vi) ORIGINAL SOURCE:
            (A) ORGANISM: HOMO SAPIENS (vii) IMMEDIATE SOURCE:
            (B) CLONE: EXON 23 BRCA1 GENE (xi) SEQUENCE DESCRIPTION: SEQ ID NO:26:

TGTGCTGACT TACCAGATGG GACAC                                                 25

```
(2) INFORMATION FOR SEQ ID NO:27:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: HOMO SAPIENS (vii) IMMEDIATE SOURCE:
        (B) CLONE: EXON 23 BRCA1 GENE (xi) SEQUENCE DESCRIPTION: SEQ ID NO:27:

GTGCTGACTT ACCAGATGGG ACACT                                        25

(2) INFORMATION FOR SEQ ID NO:28:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: HOMO SAPIENS (vii) IMMEDIATE SOURCE:
        (B) CLONE: EXON 23 BRCA1 GENE (xi) SEQUENCE DESCRIPTION: SEQ ID NO:28:

TGCTGACTTA CCAGATGGGA CACTC                                        25

(2) INFORMATION FOR SEQ ID NO:29:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: HOMO SAPIENS (vii) IMMEDIATE SOURCE:
        (B) CLONE: EXON 23 BRCA1 GENE (xi) SEQUENCE DESCRIPTION: SEQ ID NO:29:

GCTGACTTAC CAGATGGGAC ACTCT                                        25

(2) INFORMATION FOR SEQ ID NO:30:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA
```

(iii) HYPOTHETICAL: NO (vi) ORIGINAL SOURCE:
    (A) ORGANISM: HOMO SAPIENS (vii) IMMEDIATE SOURCE:
    (B) CLONE: EXON 23 BRCA1 GENE (xi) SEQUENCE DESCRIPTION: SEQ ID NO:30:

GTCATTAATG CTATGCAGAA AATCT                                              25

(2) INFORMATION FOR SEQ ID NO:31:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: HOMO SAPIENS (vii) IMMEDIATE SOURCE:
        (B) CLONE: EXON 23 BRCA1 GENE (xi) SEQUENCE DESCRIPTION: SEQ ID NO:31:

TCATTAATGC TATGCAGAAA ATCTT                                              25

(2) INFORMATION FOR SEQ ID NO:32:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: HOMO SAPIENS (vii) IMMEDIATE SOURCE:
        (B) CLONE: EXON 23 BRCA1 GENE (xi) SEQUENCE DESCRIPTION: SEQ ID NO:32:

CATTAATGCT ATGCAGAAAA TCTTA                                              25

(2) INFORMATION FOR SEQ ID NO:33:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: HOMO SAPIENS (vii) IMMEDIATE SOURCE:
        (B) CLONE: EXON 23 BRCA1 GENE (xi) SEQUENCE DESCRIPTION: SEQ ID NO:33:

ATTAATGCTA TGCAGAAAAT CTTAG                                       25

(2) INFORMATION FOR SEQ ID NO:34:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: HOMO SAPIENS (vii) IMMEDIATE SOURCE:
        (B) CLONE: EXON 23 BRCA1 GENE (xi) SEQUENCE DESCRIPTION: SEQ ID NO:34:

TTAATGCTAT GCAGAAAATC TTAGA                                       25

(2) INFORMATION FOR SEQ ID NO:35:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: HOMO SAPIENS (vii) IMMEDIATE SOURCE:
        (B) CLONE: EXON 23 BRCA1 GENE (xi) SEQUENCE DESCRIPTION: SEQ ID NO:35:

TAATGCTATG CAGAAAATCT TAGAG                                       25

(2) INFORMATION FOR SEQ ID NO:36:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: HOMO SAPIENS (vii) IMMEDIATE SOURCE:
        (B) CLONE: CYSTIC FIBROSIS GENE (xi) SEQUENCE DESCRIPTION: SEQ ID NO:36:

AAAGAAATTC TTGCTCGTTG ACCTC                                       25

(2) INFORMATION FOR SEQ ID NO:37:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: HOMO SAPIENS (vii) IMMEDIATE SOURCE:
        (B) CLONE: CYSTIC FIBROSIS GENE (xi) SEQUENCE DESCRIPTION: SEQ ID NO:37:

AAGAAATTCT TGCTCGTTGA CCTCC                                             25

(2) INFORMATION FOR SEQ ID NO:38:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: HOMO SAPIENS (vii) IMMEDIATE SOURCE:
        (B) CLONE: CYSTIC FIBROSIS GENE (xi) SEQUENCE DESCRIPTION: SEQ ID NO:38:

AGAAATTCTT GCTCGTTGAC CTCCA                                             25

(2) INFORMATION FOR SEQ ID NO:39:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: HOMO SAPIENS (vii) IMMEDIATE SOURCE:
        (B) CLONE: CYSTIC FIBROSIS GENE (xi) SEQUENCE DESCRIPTION: SEQ ID NO:39:

GAAATTCTTG CTCGTTGACC TCCAC                                             25

(2) INFORMATION FOR SEQ ID NO:40:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: HOMO SAPIENS (vii) IMMEDIATE SOURCE:
        (B) CLONE: CYSTIC FIBROSIS GENE (xi) SEQUENCE DESCRIPTION: SEQ ID NO:40:

AAATTCTTGC TCGTTGACCT CCACT                                      25

(2) INFORMATION FOR SEQ ID NO:41:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (vi) ORIGINAL SOURCE:
         (A) ORGANISM: HOMO SAPIENS (vii) IMMEDIATE SOURCE:
         (B) CLONE: CYSTIC FIBROSIS GENE (xi) SEQUENCE DESCRIPTION: SEQ ID NO:41:

TTCTTGGAGA AGGTGGAATC ACACT                                      25

(2) INFORMATION FOR SEQ ID NO:42:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (vi) ORIGINAL SOURCE:
         (A) ORGANISM: HOMO SAPIENS (vii) IMMEDIATE SOURCE:
         (B) CLONE: CYSTIC FIBROSIS GENE (xi) SEQUENCE DESCRIPTION: SEQ ID NO:42:

TCTTGGAGAA GGTGGAATCA CACTG                                      25

(2) INFORMATION FOR SEQ ID NO:43:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (vi) ORIGINAL SOURCE:
         (A) ORGANISM: HOMO SAPIENS (vii) IMMEDIATE SOURCE:
         (B) CLONE: CYSTIC FIBROSIS GENE (xi) SEQUENCE DESCRIPTION: SEQ ID NO:43:

CTTGGAGAAG GTGGAATCAC ACTGA                                      25

(2) INFORMATION FOR SEQ ID NO:44:

(i) SEQUENCE CHARACTERISTICS:
         (A) LENGTH: 25 base pairs (B) TYPE: nucleic acid
            (C) STRANDEDNESS: single
            (D) TOPOLOGY: linear (ii) MOLECULE TYPE: cDNA (iii) HYPOTHETICAL: NO (vi) ORIGINAL SOURCE:
            (A) ORGANISM: HOMO SAPIENS (vii) IMMEDIATE SOURCE:
            (B) CLONE: CYSTIC FIBROSIS GENE (xi) SEQUENCE DESCRIPTION: SEQ ID NO:44:

TTGGAGAAGG TGGAATCACA CTGAG                                              25

(2) INFORMATION FOR SEQ ID NO:45:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (vi) ORIGINAL SOURCE:
            (A) ORGANISM: HOMO SAPIENS (vii) IMMEDIATE SOURCE:
            (B) CLONE: CYSTIC FIBROSIS GENE (xi) SEQUENCE DESCRIPTION: SEQ ID NO:45:

TGGAGAAGGT GGAATCACAC TGAGT                                              25

(2) INFORMATION FOR SEQ ID NO:46:

(i) SEQUENCE CHARACTERISTICS:
            (A) LENGTH: 49 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (xi) SEQUENCE DESCRIPTION: SEQ ID NO:46:

CCAGAAGAAA GGGCCTTCAC AGTGTCCTTT ATGTAAGAAT GATATAACC                    49

(2) INFORMATION FOR SEQ ID NO:47:

(i) SEQUENCE CHARACTERISTICS:
            (A) LENGTH: 49 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (xi) SEQUENCE DESCRIPTION: SEQ ID NO:47:

CCAGAAGAAA GGGCCTTCAC AGGGTCCTTT ATGTAAGAAT GATATAACC                    49

(2) INFORMATION FOR SEQ ID NO:48:

(i) SEQUENCE CHARACTERISTICS:

(A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO:48:

GGTTATATCA TTCTTACATA AAGG                                              24

(2) INFORMATION FOR SEQ ID NO:49:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO:49:

GTTATATCAT TCTTACATAA AGGA                                              24

(2) INFORMATION FOR SEQ ID NO:50:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO:50:

TTATATCATT CTTACATAAA GGAC                                              24

(2) INFORMATION FOR SEQ ID NO:51:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO:51:

TATATCATTC TTACATAAAG GACA                                              24

(2) INFORMATION FOR SEQ ID NO:52:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO:52:

ATATCATTCT TACATAAAGG ACAC                                                      24

(2) INFORMATION FOR SEQ ID NO:53:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: HOMO SAPIENS (vii) IMMEDIATE SOURCE:
        (B) CLONE: EXON 23 BRCA1 GENE (xi) SEQUENCE DESCRIPTION: SEQ ID NO:53:

TCTTAGAGTG TCCCATCTGG TAAGTCAGCA CAAG                                           34

(2) INFORMATION FOR SEQ ID NO:54:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: HOMO SAPIENS (vii) IMMEDIATE SOURCE:
        (B) CLONE: EXON 23 BRCA1 GENE (xi) SEQUENCE DESCRIPTION: SEQ ID NO:54:

GACACTCTAA GATTTTCTGC ATAGCATTAA TGAC                                           34

(2) INFORMATION FOR SEQ ID NO:55:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: HOMO SAPIENS (vii) IMMEDIATE SOURCE:
        (B) CLONE: CYSTIC FIBROSIS GENE (xi) SEQUENCE DESCRIPTION: SEQ ID NO:55:

CTGAGTGGAG GTCAACGAGC AAGAATTTCT TT                                             32

(2) INFORMATION FOR SEQ ID NO:56:

(i) SEQUENCE CHARACTERISTICS:
        (A) LENGTH: 32 base pairs
        (B) TYPE: nucleic acid
        (C) STRANDEDNESS: single
        (D) TOPOLOGY: linear

```
        (ii) MOLECULE TYPE: cDNA (iii) HYPOTHETICAL: NO (vi) ORIGINAL SOURCE:
             (A) ORGANISM: HOMO SAPIENS (vii) IMMEDIATE SOURCE:
             (B) CLONE: CYSTIC FIBROSIS GENE (xi) SEQUENCE DESCRIPTION: SEQ ID NO:56:

TCCACTCAG TGTGATTCCAC CTTCTCCAAG AA                                  32

(2) INFORMATION FOR SEQ ID NO:57:

(i) SEQUENCE CHARACTERISTICS:
             (A) LENGTH: 11 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: YES (xi) SEQUENCE DESCRIPTION: SEQ ID NO:57:

CGGTTACCAT A                                                         11

(2) INFORMATION FOR SEQ ID NO:58:

(i) SEQUENCE CHARACTERISTICS:
             (A) LENGTH: 11 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: YES (xi) SEQUENCE DESCRIPTION: SEQ ID NO:58:

CGGTTCCCAT A                                                         11

(2) INFORMATION FOR SEQ ID NO:59:

(i) SEQUENCE CHARACTERISTICS:
             (A) LENGTH: 11 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: YES (xi) SEQUENCE DESCRIPTION: SEQ ID NO:59:

CGGTTGCCAT A                                                         11

(2) INFORMATION FOR SEQ ID NO:60:

(i) SEQUENCE CHARACTERISTICS:
             (A) LENGTH: 11 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: YES
```

-continued (xi) SEQUENCE DESCRIPTION: SEQ ID NO:60:

CGGTTTCCAT A                                                                                           11